United States Patent [19]

Wessels et al.

[11] Patent Number: 5,580,787
[45] Date of Patent: Dec. 3, 1996

[54] CLONING VECTOR FOR USE IN LACTIC ACID BACTERIA

[75] Inventors: Stephen Wessels, Gammel Strandvej 422C, DK-3060 Espergaerde; Jytte Josephsen, Magnoliavej 34, DK-2000 Frederiksberg; Finn Vogensen, Østervang 25, 1st fl., DK-3400 Hillerød; Egil W. Nielsen, Smedegade 12, DK-3500 Kirke Vaerløse, all of Denmark; Atte von Wright, Kuopio; Soile Tynkkynen, Espoo, both of Finland

[73] Assignees: Stephen Wessels, Espergaerde; Jytte Josephsen, Frederiksberg; Finn Vogensen, Hilleroed; Egil W. Nielsen, Vaerloese, all of Denmark; Valio Finnish Cooperative Dairies Association, Helsinki, Finland

[21] Appl. No.: 917,017

[22] PCT Filed: Dec. 20, 1990

[86] PCT No.: PCT/DK90/00337

§ 371 Date: Aug. 13, 1992

§ 102(e) Date: Aug. 13, 1992

[87] PCT Pub. No.: WO91/09132

PCT Pub. Date: Jun. 27, 1991

[30] Foreign Application Priority Data

Dec. 20, 1989 [DK] Denmark ............ PCT/DK89/00298

[51] Int. Cl.$^6$ ............ C12N 15/09; C12N 15/63; C12N 15/74; C12P 7/56
[52] U.S. Cl. .......... 435/320.1; 435/69.1; 435/139; 435/172.3; 435/252.3; 424/93.45
[58] Field of Search ................ 424/934, 935, 424/93.2, 93.45; 435/69.1, 252.3, 320.1, 252.9, 139, 172.3; 536/23.1, 23.2; 935/27, 72

[56] References Cited

PUBLICATIONS von Wright et al. "Isolation of a Replication Region of a Large Lactoccocal Plasmid and Use in Cloning of a Nisin Resistance Determinate" Appl. Environ. Microbiol. vol. 56, No. 7, pp. 2029–2035. Jul. 1990.
von Wright et al. 1990. Applied and Env. Microbiology vol. 56 (7): 2029–2035.
Gasson et al. 1985, FEMS Microbio. Letters 30:193–196.
Balbas et al. 1988, The Plasmid pBR322, pp. 5–8IN: Vectors; A Survey of Molecular Cloning Vectors and their Use. ed: R. Rodriguez and D. Denhardt. Butterworths, Boston.

*Primary Examiner*—John L. LeGuyader
*Assistant Examiner*—Thomas G. Larson
*Attorney, Agent, or Firm*—Anderson, Kill, Olick, P.C.

[57] ABSTRACT

A recombinant plasmid useful as a cloning vector in lactic acid bacteria and only containing DNA of lactic acid bacterial origin, the plasmid comprising (a) a DNA fragment comprising a replication region functional in lactic acid bacteria and (b) a DNA fragment comprising a marker gene selectable in lactic bacteria, the expression of which allows one-step primary selection in lactic acid bacterial cells transformed with the recombinant plasmid; a method for constructing the cloning vector plasmid; the recombinant plasmid with an inserted gene coding for a desired gene product; a method of preparing an improved food starter culture by introducing the recombinant plasmid with an inserted gene coding for a desired gene product and food starter cultures prepared by the method are provided.

21 Claims, 6 Drawing Sheets

CLONING VECTOR FOR USE IN LACTIC ACID BACTERIA

FIELD OF THE INVENTION

The present invention relates to the provision of improved lactic acid bacteria useful as food starter cultures. In particular, the invention relates to a recombinant plasmid useful as a cloning vector which is easily selectable in transformed lactic acid bacteria and a method for the construction of such a vector. Furthermore, the invention relates to the construction of improved food starter cultures comprising lactic acid bacteria into which desired genes have been introduced by means of the cloning vector and to such improved starter cultures.

GENERAL BACKGROUND OF THE INVENTION

For centuries, lactic acid bacterial cultures have been used in food production due to their ability to convert sugars by fermentation into preserving organic acids, predominantly lactic acid and various metabolic products associated with the development in the food product of a desirable taste and flavour. Some lactic acid bacteria produce hydrolytic enzymes including peptidases, proteases and lipolytic enzymes. The production of such enzymes contribute e.g. to flavour development in cheeses.

An interesting characteristic of certain lactic acid bacterial strains is their ability to produce antimicrobial compounds or bacteriocins having an inhibitory effect on closely related bacterial species. Certain lactic acid bacterial bacteriocins are applied in the food industry as preservatives.

However, for industrial production of a wide range of desired fermented food products such as all the well-known traditional dairy products including yoghurt, acidophilus milk, butter and cheeses; fermented vegetables; fermented meat products and animal feed a large range of lactic acid bacterial cultures, each of which are adapted to particular types of food products are required. Such cultures are presently being selected from naturally occurring strains of lactic acid bacteria on the basis of characteristics such as their ability to ferment sugars in the food product to be fermented, specific growth temperature requirements, production of desired flavouring compounds, the specific combination of which characteristics renders an individually selected culture useful for the production of a particular food product but normally less useful for production of others.

Obviously, this presently used procedure for developing useful lactic acid cultures by selection of naturally occurring strains is cumbersome and costly. Furthermore, it has proven difficult to provide starter culture strains which combine all the required characteristics at an optimal level. Presently, this problem is usually solved by the use of starter cultures comprising a multiplicity of selected lactic acid bacterial strains each having one or several of the characteristics desirable for a particular food product. The necessity to use such mixed cultures will of course also add to the costs in the manufacture of starter cultures.

Based on their traditional and long term application in food manufacturing and the fact that they are considered as non-pathogenic the lactic acid bacteria are generally recognized as safe food ingredients even if they are present in a fermented food product as live bacteria in a very high number.

Currently, it is widely recognized that a substantial industrial need exists to find economically and technically more feasible ways of developing starter cultures. It is obvious that gene technology may provide the means to meet this need. In the present context it is crucial that lactic acid bacteria for food starter cultures which are developed by introduction of desired genes by use of gene technology can still be recognized as safe for consumption. It is therefore essential that recombinant plasmids in order to be useful as cloning vectors in this development of lactic acid bacteria meet all the safety criteria as defined hereinbefore including the feature that such vectors only contains DNA originating from lactic acid bacteria including wild-type plasmids isolated from lactic acid bacteria. It is assumed that recombined lactic acid bacteria will still be recognized as safe for food production insofar they only contains DNA of lactic acid bacterial origin.

However, a precondition for the commercial exploitation of gene technology in the manufacturing of genetically recombined starter cultures is that such cultures would be generally recognized as safe for the consumers of food products containing live recombined lactic acid bacteria. One obvious potential risk associated with the ingestion of live recombined bacteria is the transfer of undesired genetic information herefrom to the indigenous gastro-intestinal microflora. Basically, this risk can be circumvented by constructing the recombined starter cultures in such a way that three conditions are fulfilled: (1) only DNA originating from lactic acid bacteria including wild-type plasmids isolated therefrom is introduced into the naturally occurring parent strains, (2) the inserted DNA is located on a cloning vector which essentially does not replicate in other bacterial species than lactic acid bacteria and (3) the inserted lactic acid bacterial DNA does not code for phenotypic traits which in the event they are conferred to the indigenous lactic acid bacterial flora could represent a health hazard.

The basis for the first condition is the fact that naturally occurring lactic acid cultures irrespective of their source are currently being considered as absolutely safe in food products. There has been no reports of any detrimental health effect by this traditional use of lactic acid bacteria. It is therefore generally considered that food starter cultures comprising recombined lactic acid bacterial DNA will be equally safe. The second and third conditions defined above, however, are based primarily on the consideration that mutants of naturally occurring strains of lactic acid bacteria may arise which thereby acquire undesired characteristics such as resistance to antibiotics which are used in pharmaceutical compositions useful for the treatment of infectious diseases. If such resistance phenotypes are transferred to infectious bacteria which may be present among non-lactic acid bacterial members of the human gastro-intestinal flora the treatment of such infections may become difficult. If lactic acid bacterial genes conferring resistance to pharmaceutically used antibiotics are inserted into a food starter culture there is a potential risk that such genes when the food starter-containing food is ingested might be transferred in-vivo to potentially pathogenic indigenous gastro-intestinal microorganisms.

The art of cloning foreign genes in lactic acid bacteria is still not well-developed. It is currently possible to construct recombinant strains hereof by transforming naturally occurring strains with recombinant plasmids into which desirable genes have been inserted and to obtain expression of such genes. However, the present state of the art does not provide the means of constructing recombinant starter cultures which fulfill the above-defined requirements of a safe recombined starter culture. In order to provide such safe starter cultures at least three major problems must be solved: (1) a suitable cloning vector must be provided which only contains DNA originating from a lactic acid bacterium including wild-type plasmids present herein, (2) the replication region of the cloning vector must be functional in lactic acid bacteria but preferably not in other bacterial species, in particular not in pathogenic or potentially pathogenic bacterial species, thereby reducing the risk of spreading of the vector to non lactic acid bacterial organisms to a minimum and (3) the cloning vector must be constructed in such a way that it contains a marker gene which is easily selectable in lactic acid bacteria and preferably not in other bacteria including pathogenic or potentially pathogenic gastro-intestinal bacteria, and which marker gene, should the highly unlikely event occur that the gene is transferred to a potentially harmful bacterium, would not add to the harmfulness of that bacterium e.g. by conferring resistance to a useful pharmaceutical antimicrobial agent.

Methods for the construction of cloning vectors which are functional in lactic acid bacteria are known, but vectors constructed by these known methods do not fulfill the requirements as defined above and are thus less acceptable as safe cloning means for food starter cultures.

As an example, EP 0 316 677 discloses a recombined vector which is constructed by joining a vector comprising a selectable marker which is preferably selected from genes conferring resistance to pharmaceutically applied antibiotics such as tetracycline, erythromycin and chloramphenicol and an origin of replication functional in an organism different from lactic acid bacteria such as E. coli, and a plasmid containing a replication region which is functional in lactic acid bacteria.

EP 0 228 726 discloses plasmid vectors which replicate in both gram-negative and gram-positive bacteria including lactic acid bacteria. Furthermore, the selectable markers which are used are preferably such antibiotic resistance traits which will allow selection in both gram-negative and gram-positive bacteria, a preferred selection marker being resistance to kanamycin.

A crucial step in the transformation of lactic acid bacteria with foreign DNA is the selection of transformants. Normally, the frequency of transformed cells in a transformation mixture is in the order of $10^4$–$10^6$ per µg DNA, the frequency i.a. depending on the transformation method and the amounts of DNA and recipient cells in the transformation mixture. An effective selection of a relatively low number of transformed cells among non-transformed cells the number of which in a transformation mixture typically is in the range of $10^8$–$10^{10}$ requires an extremely effective selectable marker.

In the known methods of transformation of lactic acid bacteria the selectable markers inserted in cloning vectors are selected among genes conferring resistance to antibiotics. However, in any population of recipient cells in a transformation mixture, non-transformed cells occur which by spontaneous mutation have acquired resistance to the antibiotic to which the selectable marker confers resistance. The frequency of such spontaneous mutant cells may be of the same order as the above-defined frequency of transformation. In order to obtain reliable selection of transformants on a selective medium containing the antibiotic to which transformant cells have become resistant, the level of the antibiotic must be higher than that to which spontaneous mutants are resistant. The implication hereof is i.a. that the level of resistance conferred by the selectable marker must be correspondingly higher than the level of resistance acquired by spontaneous mutations.

In the present context another essential requirement for a suitable selectable marker is that the gene(s) coding for products conferring the resistance are expressed at a sufficiently high level immediately after transformation has occurred. If this is not the case, the selection procedure will become impractically long, maybe several days and the risk that spontaneous mutants overgrow the transformed cells will increase.

As defined above, a suitable selectable marker on a cloning vector for transformation of lactic acid bacterial food starter cultures should preferably be of lactic acid bacterial origin and furthermore, it should preferably not confer resistance to antibiotics which are also used as anti-infective agents in pharmaceutical compositions. Therefore, much interest has been concentrated on markers conferring resistance to a class of antibiotics which are produced naturally by certain strains of lactic acid bacteria, viz the so-called bacteriocins. Bacteriocins of lactic acid bacterial origin are not used in pharmaceutical compositions. Among such bacteriocins the polypeptide nisin produced by certain strains of *Lactococcus* spp is the best described.

*Lactococcus* spp producing nisin comprise at the same time genes mediating resistance to this bacteriocin which genes are frequently located on plasmids (Gasson, 1984, *FEMS Microbiol. Letters* 21, 7–10). There have been several unsuccessful attempts to use nisin resistance genes as selectable markers in conjugation and transformation of such $Nis^r$ plasmids. These attempt have failed primarily due to a high frequency of spontaneously resistant mutants. (Klaenhammer and Sanozky, 1985, *J. Gen. Microbiol.* 131, 1531–1541; McKay and Baldwin, 1984, *Appl. Environ. Microbiol.* 47, 68–74).

Froseth et al., 1988, *Appl. Environ. Microbiol.* 54 2136–2139 found by studying the plasmid pNP40 isolated from *Lactococcus lactis* subsp. *lactis* biovar *diacetylactis* DRC3 that there was on this plasmid a close linkage between the $nis^r$ gene and a replication function. A 7.6 kb fragment of this plasmid which was designated pFM011 was found to replicate independently when transformed to *Lactococcus* cells. However, the $nis^r$ gene which was located on a 2.6 kb fragment was not suitable as a selectable marker since it did not allow direct or primary selection of transformants. The authors concluded that the $Nis^r$ phenotype can be used as a secondary selectable marker in cloning experiments in which direct selection is first made by using another characteristic. In their studies, this was demonstrated in co-transformation experiments by using $Ery^r$ (resistance to the pharmaceutical antibiotic erythromycin) of a shuttle vector which i.e. replicates in *E. coli* as the primary selectable marker.

Recently, the same authors have published the results of further experiments aiming at utilizing the $Nis^r$ phenotype of pFM011 as a selectable marker in transformation experiments in a *Lactococcus* sp. (*J. Dairy Sci.* 72, July 1989, Supplement 1, 115). However, selection of transformants by using the $nis^r$ gene as the sole selectable marker was only successful when a two-step procedure was applied comprising as a first step the plating of the transformation mixture onto M17-glucose agar having a pH at about 7.0 and containing either 0.25M sodium succinate or 30 international units (iu) nisin/ml, as for protoplast transformation or electroporation, respectively. After 3–5 days of incubation, a second step was carried out involving replica plating of presumptive transformants onto M17-glucose agar having a pH of about 7.0 and containing 0.1% Tween 20 and 20–40 iu nisin/ml and subsequent further incubation.

Such a two-step procedure is unlikely to be effective due to the step of replica plating which involves a considerably risk of missing the few transformant cells present on the first incubation medium. In case the first incubation medium has incorporated nisin it is furthermore likely that the activity hereof is decreased significantly during the long incubation period due to a low degree of stability of that bacteriocin at pH-values above 5–6. An other serious disadvantage is that the two-step procedure is time- and labour-consuming.

The present inventors have now succeeded in developing a recombinant plasmid which is highly suitable as a cloning vector in lactic acid bacteria for food starter cultures. The vector according to the invention fulfills all the requirements of a safe food-grade cloning vehicle as defined above and in the construction of the vector all theoretical potential risks associated with the use of gene technology in the improvement of food starter cultures have been taken into account and importantly, the cloning vector according to the invention comprises a carefully selected $nis^r$ gene conferring to the transformed lactic acid bacteria resistance at a very high level whereby it has now been made possible to use a $nis^r$ gene as a primary selectable marker in a direct one-step selection procedure.

SUMMARY OF THE INVENTION

In one aspect the present invention relates to a recombinant plasmid useful as a cloning vector in lactic acid bacteria which plasmid is capable of replicating in lactic acid bacteria but not in E.coli and B. subtilis, the plasmid comprising: (a) a DNA fragment isolated from a plasmid isolated from a lactic acid bacterium, said DNA fragment comprising a replication region functional in lactic acid bacteria but not in E. coli and B. subtilis, (b) a DNA fragment comprising a marker gene selectable in lactic acid bacteria but not in E. coli, the expression of which allows one-step primary selection of lactic acid bacterial cells transformed with a recombinant plasmid comprising said DNA fragment, the DNA fragment being isolated from a plasmid isolated from a lactic acid bacterium, and (c) at least one restriction site allowing the insertion of DNA coding for desired gene products said insertion not effecting the functions of (a) and (b), which recombinant plasmid only contains DNA originating from lactic acid bacteria including wild-type plasmids isolated therefrom.

In a further aspect, the invention relates to a method for constructing a recombinant plasmid as defined above, the method comprising as a first step the construction of a first intermediate plasmid being capable of replicating in lactic acid bacteria but not in E. coli and B. subtilis, the construction of which intermediate plasmid comprises the following substeps:

(i) isolating plasmid DNA from a lactic acid bacterium, (ii) hybridizing isolated plasmid DNA from substep (i) with a DNA fragment comprising a replication region, said DNA fragment being isolated from a wild-type plasmid isolated from a lactic acid bacterium, the wild-type plasmid being capable of replicating in lactic acid bacteria, E. coli and B. subtilis, (iii) isolating plasmid DNA from substep (i) which does not hybridize with the wild-type plasmid DNA from substep (ii), (iv) isolating from the plasmid DNA resulting from substep (iii) a DNA fragment (a) comprising a replication region functional in lactic acid bacteria but not in E. coli and B. subtilis (v) combining under ligation conditions the isolated DNA fragment from substep (iv) with a DNA fragment comprising a first selectable marker gene allowing selection of at least E. coli, B. subtilis and lactic acid bacteria transformed with a plasmid comprising said DNA fragment, to obtain the first intermediate plasmid permitting testing that the replication region of DNA fragment (a) is not functional in E. coli and B. subtilis, a second step comprising combining under ligation conditions the first intermediate plasmid with a DNA fragment (b) comprising a second marker gene being selectable in lactic acid bacteria but not in E. coli, the expression of which marker allows one-step primary selection of lactic acid bacterial cells transformed with a recombinant plasmid comprising said DNA fragment, the DNA fragment being isolated from a wild-type plasmid isolated from a lactic acid bacterium, to obtain a second intermediate plasmid, and a third step comprising deleting under restriction enzyme conditions from the second intermediate plasmid the DNA fragment comprising the first selectable marker followed by religation to obtain the recombinant plasmid useful as a cloning vector in lactic acid bacteria.

In a still further aspect the invention relates to a recombinant plasmid constructed according to the method as defined above and wherein a DNA fragment has been inserted, which inserted fragment comprises at least one gene coding for a desired gene product, said recombinant plasmid further comprising a promoter for the inserted gene. In an other further aspect the invention relates to a method of preparing a food starter culture of a lactic acid bacterium transformed with a recombinant plasmid according to the invention in which a gene capable of being expressed in lactic acid bacteria and coding for a desired gene product has been inserted and also to a food starter culture prepared according to the abovedefined method.

BRIEF DESCRIPTION OF THE DRAWINGS

FIG. 3 (parts A & B) illustrates Southern hybridization of a probe consisting of a 3.8 kb EcoRI fragment of pSW221 comprising the nisin resistance determinant isolated from pNis to various plasmids used in the invention. The probe was labelled with digoxigenin (random-primed labelling kit, Boehringer Mannheim GmbH, Penzberg, Germany). Transfer was carried out in 10×SSC onto a Gene Screen nylon membrane. A. Agarose gel (0.8%). B. Hybridization membrane.

| Lane | DNA |
|------|-----|
| 1 | lambda/HindIII |
| 2 | total plasmid of strain 10.084, not digested |
| 3 | pSF01, not digested |
| 4 | total plasmid DNA of strain 10.084, digested with HindIII |
| 5 | pSF01, digested with HindIII |
| 6 | pVS2, digested with HindIII |
| 7 | pSW211, digested with HindIII |
| 8 | pGKV10, digested with HindIII |
| 9 | pSW211, digested with EcoRI |
| 10 | pSW221, digested with EcoRI |
| 11 | pVS40, digested with EcoRI |
| 12 | pVS34, digested with EcoRI and HindIII |
| 13 | total plasmid DNA of strain 10.084, digested with EcoRI |
| 14 | pSF01, digested with EcoRI |
| 15 | lambda/HindIII |

Molecular size standards (lanes 1 and 15) are indicated at the left. The size of the HindIII Nis$^r$ fragment and its EcoRI subfragment are indicated on the right.

Figure 4:
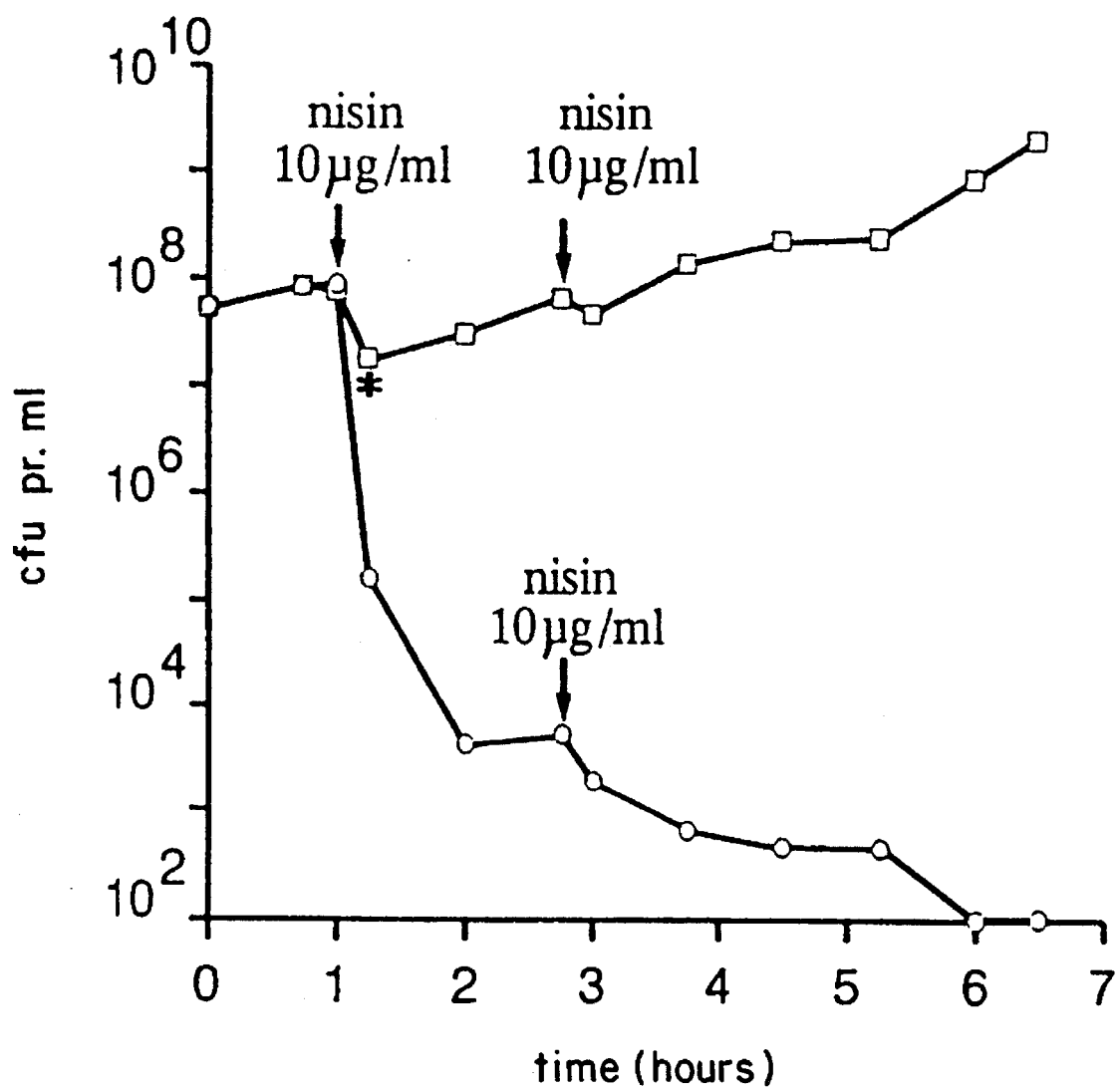

FIG. 4 illustrates the effect of nisin on exponentially growing cells with and without a nisin resistance determinant. Cultures of LMO230(pVS2) (o) and LMO230(pSW211) (□) were diluted into GM17 broth to obtain $A_600$ of 0.05. At about $A_{600}$ of 0.2 the cultures were challenged by the addition of 10 iu/ml nisin followed by a second challenge of the same size 1.5 hours later.

Figure 5:
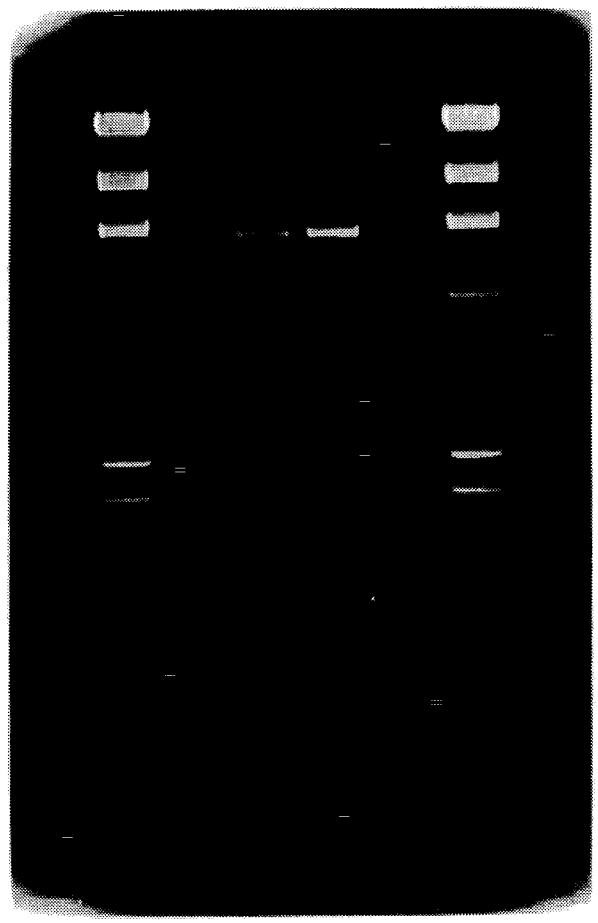

FIG. 5 is an agarose gel analysis of EcoRI fragments of two recombinant plasmids comprising pVS40 as the vector in which the BclI-B fragment of a derivative of the wild-type lactococcal plasmid pLP712 was cloned into one of the two XhoII sites in both directions. Lane A and F: lambda DNA digested with HindIII; Lane B: pVS40 digested with EcoRI; Lane C and D: two independently isolated pVS40:lac recombinant plasmids digested with EcoRI; Lane E: pLP712 digested with EcoRI.

DETAILED DISCLOSURE OF THE INVENTION

In the present context the term "lactic acid bacteria" is used to designate a taxonomically and morphologically diverse group of bacteria which are non-pathogenic, non-sporogenic microaerophilic and catalase-negative organisms, the common physiological characteristic of which is their capacity to produce lactic acid and other organic acids, including acetic acid and propionic acid from lactose and other carbohydrates by a fermentation process taking place without the presence of oxygen. The bacteria most commonly referred to as lactic acid bacteria include species of the genera *Lactococcus, Lactobacillus, Streptococcus, Pediococcus, Leuconostoc,* and *Propionibacterium*. Among *Streptococcus* spp. the most important species in the present context is *Streptococcus salivarius* subs. *thermophilus*. All of these organisms are gram-positive. The group of lactic acid bacteria does also include species of the genus *Bifidobacterium* which are generally gram-negative or gram-labile bacteria.

In addition to the production of organic acids many species of lactic acid bacteria produce desirable flavour compounds other than lactic acid. Flavour-producing lactic acid bacteria include as examples *Leuconostoc cremoris* and *Propionibacterium* spp.

Lactic acid bacterial starter cultures according to the invention are useful in the manufacturing of a large range of fermented food products including dairy products such as butter, cheeses, yoghurt and acidophilus milk; meat products including fermented sausages; fermented vegetable products such as "sauerkraut"; wines in which lactic acid bacteria have converted malolactic acid to lactic acid; bread; fermented fish products and also animal feed such as silage and fermented proteinaceous feeds for carnivorous animals.

The cloning vector according to the invention is preferably one having a replication region which enables the vector to replicate only in lactic acid bacteria. Accordingly, the present recombinant plasmid being useful as a cloning vector in lactic acid bacteria comprises a DNA fragment isolated from a plasmid isolated from a lactic acid bacterium, said DNA fragment comprising a replication region functional in lactic acid bacteria but not in *E. coli* and *B. subtilis*. By selecting a replication region which is not functional in bacteria different from lactic acid bacteria it is attempted to prevent to the highest possible degree that genetic information from ingested starter culture bacteria is transferred to indigenous non-lactic acid bacteria which are present in large numbers in the gastro-intestinal tract. This indigenous bacterial flora comprises members which are pathogenic or potentially pathogenic and it is not acceptable that such organisms acquire new phenotypes from recombined lactic acid bacteria.

In one preferred embodiment of the present invention the DNA fragment comprising a replication region being functional in lactic acid bacteria but not in *E. coli* and *B. subtilis* was isolated from a wild-type plasmid isolated from a *Lactococcus lactis* subsp. *lactis* biovar *diacetylactis* strain designated SSD207. This strain carrying the plasmid from which the DNA comprising the replication region functional in lactic acid bacteria was isolated was deposited in DSM Deutsche Sammlung von Mikroorganismen und Zellkulturen GmbH, Mascheroder Weg 1 B, D-3300 Braunschweig, Germany on 11 Dec., 1989 under the accession number DSM 5677. A deposit of the plasmids pVS 34 and pVS 39 has been made with DSM-Deutsche Sammlung von Mikroorganismen und Zelkulturen Gmbh, Mascheroder Weg 1B,D-3300 Braunschweig, Germany, on May 21, 1993. The deposited plasmid pVS 34 has been accorded the accession number DSM 8317 whereas the plasmid pVS 39 has been accorded the accession number DSM 8318.

In the context of the present invention a suitable selection marker is one which allows a direct one-step selection of transformed lactic acid bacteria occurring in a transformation mixture at a frequency which is in the range of $10^4$–$10^6$ transformants per μg DNA when the number of non-transformed cells in the transformation mixture is in the range of $10^8$–$10^{10}$ per ml of the mixture.

The most widely used selection markers in gene technology are DNA fragments comprising gene(s) mediating resistance to an antibiotic. The use of antibiotic resistance markers implies that the transformable recipient cells must be sensitive to the antibiotic to which the cloning vector confers resistance. Transformed cells having acquired such resistance genes are selected on a medium containing a level of the antibiotic which is lower than the level to which the marker confers resistance to the transformants. However, as pointed out already the occurrence in the transformation mixture of spontaneous mutants having acquired resistance to the selection antibiotic, the frequency of which mutants may be similar to or even higher than the frequency of transformation constitutes a serious problem since colonies or cultures of such resistant mutants growing in the selective medium will be indistinguishable from the transformants. The problem is particularly large in cases where only small amounts such as 10–100 ng of DNA to be transformed is available. In such cases the number of mutants growing on the selection medium may outnumber the transformed cells by a factor in the range of 10 to 100.

The present inventors have to a large extent overcome this well-known problem by isolating a selectable marker which when present on a wild-type plasmid present in a lactic acid bacterium confers to the natural host resistance to an antibiotic at a high level. As an example, a $nis^r$ gene was isolated from a plasmid naturally occurring in a *Lactococcus* sp, the growth of which was completely unaffected in the presence of 1000 iu nisin/ml medium. For comparison it may be mentioned that the $nis^r$ gene of the plasmid pFM011 disclosed by Froseth et al., Supra confers resistance at a level of only 160 iu/ml. The major advantage of using a selectable antibiotic resistance marker coding for a high level of resistance is that the span between the level of the selective antibiotic to which the spontaneous mutants are resistant and the level of the antibiotic in the selection medium may be increased whereby the probability of excluding resistant mutant cells from growing is increased significantly. In the context of the present invention it is considered advantageous that the ratio between the level of bacteriocin to which resistance is conferred by the selectable marker and the level of the bacteriocin to which at 10% of the spontaneous resitant mutants are resistant is at least 10:1, preferably at least 50:1, more preferably at least 100:1, even more preferably at least 500:1 and in particular at least 1000:1.

It is furthermore essential that the selectable marker in the vector according to the invention allows a one-step primary selection of lactic acid bacteria which have been transformed with the vector. In the present context the term "primary selection" is used to indicate that the selectable marker is expressed so effectively in the transformed cells that it can be used as the only selective marker. In several known procedures of transforming lactic acid bacteria at least two antibiotic selectable resistance markers are required, of which one which is a marker conferring resistance to a pharmaceutically useful antibiotic which marker is expressed at a high level is used as a primary selectable marker and the other one conferring resistance to a bacteriocin produced by a lactic acid bacterium is used as a secondary selectable marker. The two markers may preferably be located on two different plasmids which are then co-transferred. The primary selection is typically carried out by selecting on a medium containing the pharmaceutically useful antibiotic and subsequently a secondary selection is carried out against the other antibiotic which is therefore used as a secondary selection marker to differentiate true transformed cells from cells spontaneously resistant to the primary selection antibiotic.

Furthermore, the selectable marker on the cloning vector according to the invention is selected so as to allow that the primary selection can be carried out as a one-step procedure. In the present context, the term "one-step selection" is used to indicate that transformed cells in a transformation mixture can be detected by transferring the mixture directly to the selective medium and subsequently incubating the medium for a period of time being in the range of 6–48 hrs to allow propagation of transformants to detectable numbers. As it has been described hereinbefore (Froseth et al., supra) it is known to use resistance to a lactic acid bacterial bacteriocin as a primary selection marker in the transformation of lactic acid bacteria. However, the selection procedure disclosed by these authors was only possible when a two-step procedure was applied in which the initial step comprised a first incubation for 3–5 days followed by replica plating to a medium containing the selective bacteriocin.

An essential characteristic of a suitable selectable marker according to the invention is that the resistance is expressed constitutively. This implies that the phenotype is expressed directly without any need for induction of the gene e.g. by addition of any inducing agents.

A further feature of the cloning vector according to the invention is that it comprises at least one restriction site allowing the insertion of a DNA fragment coding for a desired gene product. A suitable restriction site is preferably a restriction site located on the vector at a site where insertion of foreign genes does not affect the functions of the selectable marker or the replication region.

In one embodiment of the invention the recombinant plasmid useful as a cloning vector is a recombinant plasmid comprising a DNA fragment comprising a replication region and a DNA fragment comprising a selectable marker, both as defined above which are isolated from different wild-type plasmids isolated from a lactic acid bacterium selected from the group consisting of species of the genera *Lactococcus*, *Lactobacillus*, *Streptococcus*, *Pediococcus*, *Leuconostoc*, *Propionibacterium* and *Bifidobacterium*.

In a preferred embodiment the recombinant plasmid cloning vector according to the invention is a plasmid wherein the marker gene being selectable in lactic acid bacteria but not in *E. coli* is a marker which confers to the transformed cells resistance to a bacteriocin produced by a lactic acid bacterium. Bacteriocins are proteins or protein complexes having bactericidal activity directed against species that are usually closely related to the producer bacterium. The range of inhibitory activity by bacteriocins of lactic acid bacteria can be either narrow, inhibiting only species which are closely related to the producer organism, or wider, inhibiting a more diverse group of gram-positive organisms e.g. including *Bacillus* spp, *Listeria* spp and *Clostridium* spp. The most studied lactic acid bacterial bacteriocin is nisin which is produced by certain strains of *Lactococcus lactis*. Nisin belongs to a group of bacteriocins which have in common a high proportion of the amino acids lanthionine and β-methyllanthionine. Other examples of bacteriocins from lactic acid bacteria are lactostrepcin and diplococcin both produced by *Lactococcus lactis* subsp. *cremoris* and pediocins produced by *Pediococcus* spp.

Thus, when selecting a useful selectable marker, the present inventors appreciated that a lactic acid bacterium producing a bacteriocin must be inherently insensitive to that bacteriocin. It is known that the level of this insensitivity or resistance is highly variable as it has been described hereinbefore. However, the inventors have realized that a selectable bacteriocin resistance marker allowing a one-step primary selection might preferably be isolated from a lactic acid bacterium producing the selective bacteriocin in large amounts. Accordingly, as an initial step in the isolation of a suitable selectable marker as defined above, strains of lactic acid bacteria producing a bacteriocin in large amount were selected and tested for resistance to the produced bacteriocin.

As an example, one strain of *Lactococcus lactis* subsp. *lactis* designated 10.084 was completely resistant to 1000 iu/ml nisin and even at 3000 iu/ml the growth of the strain was only slightly influenced. From this strain a plasmid could be isolated which conferred the resistance to a sensitive lactic acid bacterium. The plasmid was originally designated pNis but has subsequently been given the designation pSF01. The *Lactococcus lactis* subsp. *lactis* 10.084 strain comprising pNis/pSF01 was deposited in DSM Deutsche Sammlung von Mikroorganismen und Zellkulturen GmbH, Mascheroder Weg 1 B, D-3300 Braunschweig, Germany on 11 Dec., 1989 under the accession number DSM 5678.

Accordingly, in one preferred embodiment of the invention there is provided a recombinant plasmid useful as a cloning vector in lactic acid bacteria wherein the selectable marker allowing one-step primary selection is a nisin resistance marker genetic determinant conferring resistance to a transformable nisin sensitive lactic acid bacterium at a level which is at least 200 iu/ml nisin, preferably at least 500 iu/ml, more preferably at least 1000 iu/ml, even more preferably at least 2000 iu/ml and in particular at least 3000 iu/ml, the resistance being determined as the minimum inhibitory concentration in a liquid medium allowing optimal growth of lactic acid bacteria.

In a further preferred embodiment of the invention the recombinant plasmid cloning vector is the plasmid pVS40 which was deposited in DSM Deutsche Sammlung von Mikroorganismen und Zellkulturen GmbH, Mascheroder Weg 1 B, D-3300 Braunschweig, Germany on 11 Dec., 1989 under the accession number DSM 5679, in the form of a transformed derivative of *Lactococcus lactis* subsp. *lactis* NCDO 712 being designated MG1614(pVS40) or other plasmids only containing DNA originating from lactic acid bacteria including wild-type plasmids therefrom and which comprises a selectable marker and a replication region having essentially the characteristics of the selectable marker and the replication region of pVS40. It will be understood that the selectable marker and the replication region may be isolated from any lactic acid bacterium as defined hereinbefore.

A useful recombinant plasmid according to the invention is preferably a plasmid having a size which is in the range of 1–20 kbp, more preferably in the range of 2–15 kbp and in particular in the range of 3–10 kbp such as about 7.8 kbp.

In another aspect, the invention relates to a method for constructing a recombinant plasmid cloning vector as defined in details above. The method comprises as a first step the construction of a first intermediate plasmid being capable of replicating in lactic acid bacteria but not in *E. coli* and *B. subtilis*. Appropriate and useful procedures for the isolation of a DNA fragment of lactic acid bacterial origin and comprising a replication region coding for the defined replication behaviour were not available. The present inventors, however contemplated that the replication region searched for most probably could be isolated from a plasmid, the DNA of which did not hybridize with replication region DNA of a broad host range plasmid capable of replicating in at least lactic acid bacteria, *E. coli* and *B. subtilis*.

Accordingly, the construction of the first intermediate plasmid comprises the following substeps:

(i) isolating plasmid DNA from a lactic acid bacterium, (ii) hybridizing the isolated plasmid DNA from substep (i) with a DNA fragment comprising a replication region said DNA fragment being isolated from a wild-type plasmid isolated from a lactic acid bacterium and being capable of replicating in lactic acid bacteria, *E. coli* and *B. subtilis*, (iii) isolating plasmid DNA from substep (i) which does not hybridize with the wild-type plasmid DNA from substep (ii), (iv) isolating from the plasmid DNA resulting from substep (iii) a DNA fragment (a) comprising a replication region functional in lactic acid bacteria but not in *E. coli* and *B. subtilis*, (v) combining under ligation conditions the isolated DNA fragment from substep (iv) with a DNA fragment comprising a first selectable marker gene allowing selection of at least *E. coli*, *B. subtilis* and lactic acid bacteria transformed with a plasmid comprising said DNA fragment, to obtain the first intermediate plasmid permitting testing that the replication region of DNA fragment (a) is not functional in *E. coli* and *B. subtilis*.

The transformation experiments are disclosed in details in the below examples.

The use of a first selectable marker gene as defined above is essential since its broad range selectability makes it possible to test the replication behaviour of the selected replication region. This testing is carried out by attempting transformation of strains of at least lactic acid bacteria, *E. coli* and *B. subtilis* with the intermediate plasmid. A negative outcome of such transformation experiments is considered as an indication that the selected replication region of the intermediate plasmid is not functional. In the experiments replication of the intermediate plasmid was observed in e.g. *Lactobacillus plantarum* and *Lactococcus lactis* spp but not incompetent recipient *E. coli* and *B. subtilis*. In the art it is generally considered that unsuccessful transformation experiments when using competent recipient cells are clear indications of lack of replication capability of the DNA tested.

In a preferred embodiment of the invention the DNA fragment comprising a replication region being capable of replicating in lactic acid bacteria but not in *E. coli* and *B. subtilis*, is isolated from a wild-type plasmid isolated from *Lactococcus lactis* subsp. *lactis* biovar *diacetylactis* in particular *Lactococcus lactis* subsp. *lactis* biovar *diacetylactis* SSD207.

The method comprises further a second step comprising combining under ligation conditions the first intermediate plasmid with a DNA fragment (b) comprising a second marker gene being selectable in lactic acid bacteria but not in *E. coli*, the expression of which marker allows one-step primary selection of lactic acid bacterial cells transformed with a recombinant plasmid comprising said DNA fragment, the DNA fragment being isolated from a wild-type plasmid isolated from a lactic acid bacterium, to obtain a second intermediate plasmid. The characteristics of the second selectable marker which is preferred in the second step are those which have been defined hereinbefore. The detailed applicable procedures have been exemplified in details in the below examples.

A third step of the method comprises deleting under restriction enzyme conditions from the second intermediate plasmid the DNA fragment comprising the first selectable marker followed by religation to obtain a recombinant plasmid useful as a cloning vector in lactic acid bacteria.

In a preferred embodiment of the method the selectable marker gene according to the invention confers to the transformed cells resistance to a bacteriocin produced by a lactic acid bacterium, in particular to nisin. Furthermore, the selectable nisin resistance marker gene preferably confers resistance to at least 200 iu/ml nisin, preferably to at least 500 iu/ml, more preferably to at least 1000 iu/ml, even more preferably to at least 2000 iu/ml and in particular to at least 3000 iu/ml. As one example the DNA fragment (b) is isolated from a wild-type plasmid isolated from *Lactococcus lactis* subsp. *lactis* 10.084

Figure 1A:
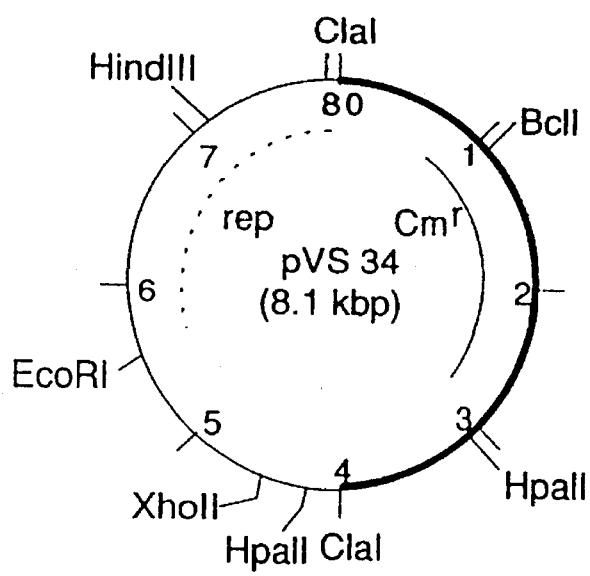
FIG. 1A is a partial restriction map of an intermediate plasmid pVS34. The bold line indicates DNA from pVC5 and the thin line DNA derived from a plasmid isolated from *Lactococcus lactis* subsp *lactis* biovar *diacetylactis* SSD207

An example of a particularly useful recombinant plasmid cloning vector resulting from the method is pVS40. As it is illustrated in FIG. 1, pVS40 is constructed by using pVS34 as the first intermediate plasmid and pVS39 as the second intermediate plasmid.

In a still further aspect the invention relates to a recombinant plasmid cloning vector as defined above wherein a further DNA fragment has been inserted, which inserted DNA fragment comprises at least one gene coding for a desired gene product, and a promoter therefor which is functional in a lactic acid bacterium. Preferably, the gene coding for a desired gene product is isolated from a lactic acid bacterium including plasmids contained therein.

In the context of the present invention a desired gene product may be any product the expression of which confers a useful phenotype to a lactic acid bacterium which is used as a food starter culture. Such gene products may be e.g. be selected from the group consisting of enzymes, bacteriocins and gene products conferring phage resistance. It may be of interest in the improvement of starter cultures to introduce the cloning vector comprising the inserted desired gene even in starter culture strains where the conferred phenotype is already present in order to enhance the expression hereof.

Examples of useful enzymes are lipases, peptidases, meat tendering enzymes, pectinases, lysozyme, proteases, galactosidases and other enzymes enabling the starter culture strain to metabolize carbohydrates including enzymes which when expressed in the presence of lactose results in the formation of lactic acid. Desired flavour compounds the production of which may be coded for by an inserted gene are e.g. acetoin and diacetyl. The recombinant plasmid according to the invention may also be useful in production of bacteriocins. Accordingly, the inserted gene may comprise DNA coding for bacteriocin production. An important characteristic of useful food starter cultures is resistance to bacteriophages. The mechanisms behind phage resistance are well-known and the genetic determinants are also known. As an example resistance to bacteriophages may be the result of the production by the resistant bacterium of restriction enzymes. It is contemplated that the recombinant cloning vector according to the invention will be useful in conferring phage resistance phenotypes to phage sensitive lactic acid bacteria. A still further example of a useful phenotype which may be conferred to a starter culture is temperature tolerance of the host organisms. In the production of certain fermented food products it may be advantageous to carry out the fermentation process within a particular temperature range.

In addition to insertion of genes coding for desired gene products in lactic acid bacteria which are useful in food starter cultures it will be appreciated that the recombinant vector according to the invention may be useful also for construction of vectors having inserted genes coding for other useful products such as pharmaceutically or technologically active polypeptides including as examples interferons, insulin or chymosin. Further examples of useful genes are genes coding for the production of amino acids or vitamins.

The level of expression of a desired product encoded by the inserted gene will i.a. depend on the number of copies of the recombinant plasmid cloning vector. It is known from bacteria other than lactic acid bacteria that plasmids may occur in high copy numbers as a result of certain mutations or there may be constructed high copy number plasmids from low copy number wild-type plasmids by inserting genes coding for high copy number. The present inventors have carried out experiments the result of which indicate that recombinant plasmids according to the invention may be modified by mutagenization to occur in an increased copy number. It has thus been demonstrated that the replication region of plasmid pVS39 can be modified by in-vitro mutagenization with $NH_4OH$. When a chloramphenicol sensitive ($Cm^s$) recipient strain of a *Lactococcus* sp. is transformed with pVS39 comprising the mutagenized replication region these transformants showed a minimum inhibitory concentration against Cm of 100 µg/ml. In comparison, the same recipient strain transformed with pVS39 comprising the parent replication region acquired resistance to at the most 25 µg/ml Cm. Although these results are not conclusive evidence that the thus modified pVS39 occur in an increased copy number, they provide strong indications that this is the case. It is generally known in the art that the most likely mechanism behind increased tolerance to chloramphenicol in a bacterium is an increased dosage of the DNA coding for the resistance.

When applying a food starter culture based on lactic acid bacteria having been transformed with a recombinant plasmid according to the invention comprising an inserted gene as defined above it is desirable that the plasmid is stably maintained during the food fermentation process which process involves that the starter culture bacteria are propagated. It is therefore contemplated that the present recombinant plasmids may be further improved by e.g. inserting genes into the plasmids which code for a partitioning function. Such a function which is well described in e.g. *E. coli* has the effect that all progeny of a plasmid-containing host bacterium will contain the plasmid.

In another aspect the present invention relates to a method of preparing a recombinant plasmid as defined above wherein a further DNA fragment has been inserted, which inserted DNA fragment comprises at least one gene coding for a desired gene product, and a promoter therefor which is functional in a lactic acid bacterium comprising inserting into a restriction site of a recombinant plasmid according to the invention a gene coding for a desired gene product, and optionally a promoter therefor which is functional in a lactic acid bacterium. The promoter may be one which is inherently present in the plasmid or it may optionally be a foreign promoter which is functional in lactic acid bacteria and which is inserted together with the desired gene. Examples of promoters which are functional in lactic acid bacteria are strong promoters for *Lactococcus lactis* subsp. *cremoris* being isolated from *Lactococcus lactis* spp. as disclosed by Jos et al. 1987 (*Appl. Environ. Microbiol.* 53, 2452–2457 and promoters for i.a. *Lactococcus lactis* isolated from a *Lactoccus lactis* subsp. *cremoris* temperate bacteriophage as disclosed by Lakshmidevi et al. 1990 (*Appl. Environ. Microbiol.* 56, 934–942.

It is essential that the selected site of insertion is located on the recombinant plasmid at a position where the insertion does not affect the function of the replication region and the selectable marker determinant. Preferably the selected site may be a unique restriction site but other sites may also be applicable.

In still an other aspect of the invention there is provided a method of preparing a food starter culture of a lactic acid bacterium comprising the transformation of a lactic acid bacterium with a recombinant plasmid as defined herein into which a desired gene has been inserted, selecting a transformed lactic acid bacterium, cultivating the selected transformant, isolating the cultured transformed cells and preparing a food starter culture herefrom.

The transformation is carried out according to methods which are known per se such as protoplast transformation or electroporation and which are described and exemplified in the below examples. When the recombinant plasmid is one comprising as the primary selectable marker a bacteriocin resistance determinant, transformants are selected in a medium containing the bacteriocin, preferably in an amount resulting in a proportion hereof which is close to the level to which the selectable marker confers resistance. However, newly transformed cells may temporarily be more susceptible to the bacteriocin. Accordingly, it may be necessary to select transformants at a level which is less than the minimum inhibitory concentration. As an example, the nisin resistance determinant of the plasmid pVS40 confers resistance to at least 1000 iu/ml when present in host cells not newly transformed, whereas the resistance of lactic acid bacterial cells newly transformed with the plasmid may be reduced by a factor in the range of 2–20.

Accordingly, when practicing the method of preparing a food starter culture of lactic acid bacteria the step of selecting transformed cells may preferably be carried out using nisin as the selective bacteriocin at a concentration in the selection medium which is at least 50 iu/ml, preferably at least 75 iu/ml, more preferably at least 100 iu/ml and in particular at least 500 iu/ml.

The cultivation of a transformed cells and the downstream processes resulting in final starter culture products are carried out according to methods which are well-known in the food starter culture industry.

The invention relates also to a food starter culture comprising a culture of a lactic acid bacterium prepared according to the above disclosed method. In the present context the term "food starter culture" is used to describe a composition comprising as an essential part one or more strains of lactic acid bacteria comprising a recombinant plasmid according to the invention, the composition being intended for fermentation of a particular food product. A food starter culture as defined may e.g. be a dairy starter culture, a meat starter culture, a bread starter culture, a wine malolactic culture, a silage culture or a vegetable starter culture. Within all of these starter culture types there may be subtypes comprising lactic acid bacteria comprising recombinant plasmids having inserted genes making the resulting subtype of starter culture specifically useful in the production of a particular food product. Thus, within dairy starter cultures according to the invention there may be yogurt starter cultures or cheese starter cultures.

The starter culture may be in the form of liquid composition such as a fermented milk which optionally is in a frozen form or in dried e.g. as a freeze-dried powder.

The food starter culture may comprise any suitable lactic acid bacterium prepared according to the invention. Preferably the lactic acid bacteria are selected from a group consisting of *Streptococcus* spp, *Lactococcus* spp, *Lactobacillus* spp, *Bifidobacterium* spp, *Leuconostoc* spp, *Propionibacterium* spp and *Pediococcus* spp.

The invention is described in further details in the following examples.

EXAMPLES

Materials and Methods

Bacterial strains, plasmids, media and culture conditions

Figure 3A:

*Lactococus lactis* subsp. *lactis* biovar. *diacetylactis* SSD207 is isolated from a dairy starter culture. In gel electrophoresis it shows at least 12 plasmid bands ranging in size from 2 to more than 30 kbp [von Wright et al., *Lett.* *Appl. Microbiol.* 2, 73–76 (1986)]. *Lactococcus lactis* subsp. *lactis* 10.084 was obtained from the strain collection maintained at the Danish Government Research Institute for Dairy Industry. This strain carries 5 or 6 plasmids, as illustrated in FIG. 3A, lane 13. Recipient strains and different plasmids used in the transformation and cloning experiments are detailed in table I. M17 medium [Terzaghi, B. E. and Sandine, W. E., *Appl. Microbiol.* 29, 807–813 (1975)]; Difco, East Molesey, UK), supplemented with either 0.5% lactose (for SSD207, 10.084 and strains carrying the plasmid pNis/pSF01) or glucose (for the rest of the strains) was used in experiments with *L. lactis* subsp. *lactis* and *Staphylococcus aureus*. *Escherichia coli* and *Bacillus subtilis* were grown in L-broth or L-agar, as defined in Maniatis et al., Molecular Cloning: A laboratory Manual. Cold Spring Harbor Laboratory, Cold Spring Harbor, N.Y. (1982). MRS-medium (DeMan, J. C. et al., *J. Appl. Bact.* 23, 130–135 (1960) was used in experiments with *Lactobacillus plantarum*. The incubation temperature was 32° C. for Lactococcus spp., 30° C. for *L. plantarum* and 37° C. for the others species.

The strain MG1614, a derivative of *L. lactis* subsp. *lactis* NCDO712, which has been cured of plasmids and prophages following several rounds of protoplast curing was obtained from M. Gasson. The strain LM0230, received from L. L. McKay is described as a derivative of *L. lactis* subsp. *lactis* C2, which has been cured of plasmids and prophages as a result of treatment with nitrosoguanidine and ultraviolet radiation. The mixed strain starter cultures BOLL1 and D1 are both produced by Chr. Hansen's Laboratory Ltd., Hørsholm, Denmark, and both are used routinely in production at the Danish Government Research Institute for Dairy. BOLL1, widely used in the production of cheese, is a Direct Vat Set (freeze-dried) dairy starter culture reported to contain approximately 1–5% *L. lactis* subsp. *lactis*, 70–75% *L. lactis* subsp, *cremoris*, and 2–5% *Leuconostoc cremoris* (Chr. Hansens's Laboratorium Ltd., Declaration of mesophilic lactic ferment cultures).

Media and culture conditions

For the detection of lactose or sucrose fermentation phenotypes, the bromocresol purple indicator of McKay et al., *Appl. Microbiol*, 23, 1090–1096 (1972), was supplemented with 1% lactose or sucrose, respectively. The proteinase phenotype was tested by inoculating one colony into 10 ml autoclaved reconstituted skim milk supplemented with 0.5% glucose and 0.1% litmus. After incubation for 24 h at 30° C., a clone causing decoloration of the litmus and coagulation of the milk was considered to be proteinase-positive. To determine whether strains were nisin producers, the agar flip-over method of Scherwitz et al., *Appl. Environ. Microbiol.* 45, 1506–1512 (1983), was employed using LM0230 as the indicator organism. For routine detection and selection of the nisin resistance determinant, nisin was added at 100 iu/ml to solid media. The antibiotics chloramphenicol (Cm) and erythromycin (Em) were added to final concentrations of 5 and 2.5 µg per ml, respectively.

For measurements of growth in broth, $A_{600}$ was monitored using a Spectronic 501 spectrophotometer (Milton Roy Corp.), and viable cells were counted [colony forming units (cfu) per ml] by plating appropriate dilutions on GM17 agar.

To determine single-cell resistance to nisin, approximately 105 cfu of an exponentially growing culture in GM17 broth were spread onto freshly prepared GM17 plates and GM17 plates containing concentrations of nisin ranging from 10 to 3000 iu/ml. The plates were incubated for 24 h, after which the approximate number of colonies on each plate was estimated relative to the plates without nisin.

TABLE I

| Strain | Relevant phenotype[a] | Description and reference |
|---|---|---|
| Lactococcus lactis subsp. lactis biovar. diacetylactis SSD207 Lactococus lactis subsp. lactis | Lac+ Prt- | Lett. Appl. Microbiol. 2. 73–76 (1986) |
| 10.084 | Nip+ Nis+ Lac+ Suc+ Prt+ | The strain collection of the Danish Government Research Institute for Dairy Industry |
| MG1614 | Nis$^s$ Rif$^r$ Str$^r$ | Plasmid-free derivative of L. lactis subsp. lactis NCDO 712; J. Bacteriol. 154, 1–9 (1983) |
| LM0230 | Nis$^s$ | Plasmid free derivative of L. lactis subsp. lactis C2; Appl. Environ. Microbiol. 32, 45–52 (1976) |
| MG1614(pNis) | Nip+ Nis$^r$ Lac$^r$ Suc- Prt+ Rif$^r$ Str$^r$ | This invention (second-round transformant by plasmids of strain 10.084) |
| MG1614(pSW211) | Nis$^r$ Cm$^r$ Em$^r$ Rif$^r$ Str$^r$ | |
| MG1614(pSW221) | Nis$^r$ Em$^r$ Rif$^r$ Str$^r$ | |
| ML0230(pSW211) | Nis$^r$ Cm$^r$ Em$^r$ | |
| ML0230(pSW221) | Nis$^r$ Em$^r$ | |
| E. coli AB259 | thi | Mol. Gen. Genet. 127, 47–55 (1973) |
| B. subtilis 3G18 | Ade, Met, Trp | Gerard Venema, the University of Groningen, the Netherlands |
| S. aureus RN451 | | Richard Novick, the Public Health Research Institute of the City of New York, Inc., New York |
| Lb. plantarum 755 | Contains a cryptic plasmid of about 37 kbp | The strain collection of the Research and Development Centre of Valio Finnish Cooperative Dairies |

| Plasmid | Phenotype | Size (kbp) | Description and Reference |
|---|---|---|---|
| pBR322 | Amp$^r$ Tet$^r$ | 4.3 | Gene 2, 95–113 (1977) |
| pVC5 | Amp$^r$ Cm$^r$ Tet$^r$ | 8.4 | The 4.1 kbp ClaI fragment containing the chloramphenicol resistance gene of pGB301, Mol. Gen. Genet. 184, 115–120 (1981). cloned to the single ClaI site of pBR322 (S. Tynkkynen, M.Sc. Thesis, 1985, University of Helsinki, Helsinki, Finland |
| pVS1 | Cm$^r$ | 4.5 | The 2.8 kbp ClaI-HpaII fragment of pVC5 cloned on the 1.7 ClaI fragment of pSH71; J. Bacteriol. 154, 1–9 (1983) (S. Tynkkynen, M.Sc. thesis) |
| pNis | Nip+ Nis$^r$ Lac+ Suc- Prt+ | 46 | This invention |
| pVS2 | Cm$^r$ Em$^r$ | 4.9 | Appl. Environ. Microbiol. 53, 1584–1588 (1987) |
| pSW211 | Cm$^r$ Em$^r$ Nis$^r$ | 12.8 | This invention (pVS2::Nis$^r$/HindIII) |
| pGKV10 | Em$^r$ | 4.6 | Appl. Environ. Microbiol. 50, 540–542 (1985) |
| pSW221 | Em$^r$ Nis$^r$ | 8.4 | This invention (pGKV10::Nis$^r$/EcoRI) |
| pVS34 | Cm$^r$ | 8.1 | This invention |
| pVS39 | Cm$^r$ Nis$^r$ | 11.8 | This invention |
| pVS40 | Nis$^r$ | 7.8 | This invention |

[a]Abbreviation: Nip+, Nisin-production positive; Nis$^r$, nisin resistant; Lac+, lactose fermenting; Suc+, sucrose fermenting; Prt+, proteinase-production positive; Rif, rifampin: Str, streptomycin; Cm, chloramphenicol; Em, erythromycin; Tet, tetracycline; s, sensitive; r, resistant Ade, Met, Trp, adenine methionine tryptophan auxotroph.

Nisin solutions

Nisin was applied in the the form of the commercial product Nisaplin, which is manufactured by Aplin and Barrett Ltd., Trowbridge, Wilts., England. According to the manufacturer, the major components of Nisaplin are milk proteins (17.12%), carbohydrate (5.9%) and NaCl (74.7%), plus nisin at 1026 units pr. mg (Aplin and Barrett, pamphlet accompanying product). Since the specific activity of nisin is so close to 1000 units per mg, the iu-values of nisin activity referred to in the specification are approximately equivalent to μg of Nisaplin and accordingly references to concentrations of nisin are synonymous with Nisaplin concentrations. Stock solutions of nisin were prepared by dissolving Nisaplin at 10 mg pr. ml in 0.02 N HCl and were in no further way sterilized.

Frequency of spontaneous nisin resistant mutants

The frequency of spontaneous nisin resistance mutants was determined for the plasmid-free lactococcal strains MG1614 and LM0230. Cells of each strain grown in GM17 broth were harvested by centrifugation, resuspended in a volume of sterile, distilled water corresponding to one-tenth of the starting volume and plated in appropriate dilutions on GM17 agar containing 0, 100 and 1000 iu nisin pr. ml. Colonies were counted after incubation for 24 h and 48 h.

Frequency of nisin resistant organisms occurring in commercial dairy starter cultures In order to mimic dairy practice with respect to reactivation of each freeze-dried starter product, 0.158 g and 1.01 g of BOLL1 and D1, respectively were weighed aseptically, inoculated into 1 L of freshly autoclaved reconstituted skim milk and incubated at 30° C. for 3 h. Then dilutions were plated on GM17 plates either without nisin or containing 100 and 1000 iu/ml nisin. The plates were incubated for 24 h before the number of colonies was counted.

Plasmid DNA isolation and molecular cloning

For both small-scale and preparative isolation of plasmid DNA, the method of Anderson and McKay, *Appl. Environ. Microviol.* 46, 549–552 (1983), was used. For preparative purposes the lysate was further purified by cesium chloride-ethidium bromide density gradient ultracentrifugation. All restriction mapping was conducted using gradient-purified DNA. Concentrations of DNA were evaluated according to the agarose plate method suggested by Maniatis et al., supra.

All cloning was done employing DNA isolated either from strain MG1614 or LM0230, and the ligation mixtures in each case were transformed into MG1614. Then small-scale preparations of transformant DNA were retransformed into either MG1614 or LM0230. Restriction endonucleases, calf intestine phosphatase, and T4-DNA ligase (all from Boehringer Mannheim GmbH) and Gene Clean (Bio 101, Inc.) were applied according to the instructions by the manufacturer.

Transformation

In the construction of pVS34, pVS39 and pVS40, *L. lactis* subsp. *lactis* MG1614 protoplasts were transformed according to the method described in *Appl. Environ. Microbiol.* 50, 1100–1102 (1985). The method of Mandel and Higa (*J. Mol. Biol.* 53, 159–162 (1970)) was used to transform *E. coli* AB259. Chloramphenicol (5 µg/ml) was used as the selection agent with MG1614, and, either alone or together with ampicillin (at concentrations of 5 and 50 µg/ml, respectively), with *E. coli*. The nisin resistance phenotype of chloramphenicol-resistant MG1614 transformants was checked on agar containing 500 iu/ml of a nisin-preparation.

For the isolation of the nisin resistance determinant protoplast transformation was carried essentially according to von Wright et al., *Appl. Environ. Microbiol.* 50, 1100–1102, with the following modifications: Strains to be transformed were diluted 20 times from a fresh overnight culture into GM17 broth and incubated for 3 h at 30° C. This culture was then diluted 1000 times into ice cold GM17 broth, kept on ice overnight and subsequently grown at 30° C. for about 5 h prior to harvesting at $A_{600}$ 0.4. 0.5M sucrose [household granulated (pearl) sugar, The Danish Sugar Corp., Copenhagen, Denmark] was used as an osmotic stabilizer, and all water used was freshly glass-distilled. Protoplasting proceeded in GM17S-SAM (M17 broth and 0.5M sucrose, autoclaved; 0.5% glucose, 1 mM Mg acetate, 4 mM $NH_4$ acetate, pH 7.0, filter-sterilized). A 10 ml culture volume of the strain MG1614 was treated with 4 mg pr. ml lysozyme (Sigma, St. Louis, MO, grade I) at 37° C. for 15 min, while 10 ml of LM0230 was protoplasted in 1 mg pr. ml lysozyme at 37° C. for 15 min. Hereafter all manipulations were carried out at ambient temperature. Protoplasts were washed once in the transformation buffer SMMC (0.5M sucrose, 20 mM $Na_2$ maleate, 20 mM MgC12, 50 mM $CaCl_2$, pH 6.5 filter sterilized) and finally resuspended in 500 µl SMMC.

Each transformation mixture contained DNA made up to 10 µl in TE buffer (10 mM Tris-HCl, pH 8.0; 1 mM EDTA), 10 µl 2×SMMC, 50 µl protoplasts and 210 µl 30% PEG 3350 (Polyethylene glycol MW 3350, Sigma, dissolved in 1×SMMC and filter sterilized). PEG treatment lasted for 20 min, and phenotypic expression was carried out for 2 h in GM17S. The entire mixture was distributed onto selective plates and overlayed with 5 ml M17S soft agar (0.7% agar). After incubation for 24 h at 30° C., the plates were evaluated.

For evaluating the efficiency of selection of the studied $Nis^r$ determinant relative to $Cm^r$ (chloramphenicol resistance) in pSW 211 and pVS39 electroporation was used conducted according to the method described by Holo and Nes, 1989, *Appl. Environ. Microbiol.* 55, 3119–3123.

Selection for $Cm^r$, $Em^r$ (Erythromycin resistant) and $Nis^r$ transformants was conducted on GM17S plates at concentrations of 5, 2.5 og 100 µg pr. ml, respectively.

Competent cells of *B. subtilis* were transformed according to the method of Boylan et al., *J. Bacteriol.* 110, 281–290 (1972). Chloramphenicol (5 µg/ml) was used for the selection. To check the effects of multimeric forms of plasmids on the transformation frequencies, plasmids were linearized with suitable restriction enzymes (HindIII with pVS2, and EcoRI with pVS34) and religated before transformation, using untreated plasmids as controls.

*L. plantarum* and *S. aureus* were transformed by electroporation. A fresh inoculum using cells grown overnight was made in the appropriate broth to give an absorbance of 0.15–0.18 at 600 nm. The cultures were grown until the absorbance reached 0.5–0.7 and the cells were harvested by centrifugation at 4° C., washed twice and finally suspended in electroporation buffer (272 mM sucrose, 15% glycerol) corresponding to 1/20 of culture volume. The electroporation mixture (200 µl of cell suspension held in ice for two minutes in an electroporation cuvette with a 2 mm electrode gap, to which is added up to 20 µl purified plasmid DNA in 10 mM Tris-HCL, 1 mM EDTA, pH 7.5) was given a single electric pulse in a Genepulser™ apparatus (Bio-Rad Laboratories, Richmond, Calif., U.S.A.). The capacitance was 25 *F and the voltage either 2 kV (*L. plantarum*) or 2.5 kV (*S. aureus*). The cuvette was connected in parallel to a 1000 ohm (*L. plantarum*) or 600 ohm (*s. aureus*) resistor (Bio-Rad Pulse Controller). The cells were then kept in ice for 2 minutes, suspended in 10 ml prewarmed culture broth, incubated for 1–2 h and harvested by centrifugation of 9 ml at room temperature, the pellet being resuspended in the remaining 1 ml. The suspension was spread on selection plates containing either 10 µg (for *L. plantarum*) or 5 µg (for *S. aureus*) chloramphenicol per ml. *L. plantarum* plates were incubated anaerobically at 30° C. for 48 h, while aerobic conditions and 37° C. for 24–48 h were applied to *S. aureus*.

*Plasmid elimination.* Novobiocin gradient plates were used for plasmid elimination as described previously, *Appl. Environ. Microbiol.* 53, 1385–1386 (1987).

Southern hybridization. For the construction of pVS34, DNA was transferred to a nitrocellulose filter (Sleicher & Schuell, Dassel, FRG) using standard techniques, Leary et al., *Proc. Natl. Acad. Sci. USA* 80, 4045–4049 (1983). The biotin-labelled probe was prepared using BRL Nick Translation Reagent kit (Bethesda Research Laboratories Inc., Gaithersburg, Md., U.S.A.) and biotinylated dUTP (Boehringer GmbH, Mannheim, FRG). The staining was performed with Vectastain ABC Alkaline Phosphatase kit (Vector Laboratories Inc., Burlingame, Calif., U.S.A.) according to the instructions of the manufacturer.

To demonstrate the derivation of the nisin resistance determinant, transfer of DNA from an 0.8% agarose gel (HGT agarose, SeaKem, Rockland, ME) run in TAE buffer (Maniatis et al.,Supra ) to a Gene Screen nylon membrane (NEN Research Products, Boston, Mass.) was achieved by using the method of Southern, as described by Maniatis et al., supra.

The template DNA for the probe was prepared by sequentially digesting about 0.6 µg pSW221 DNA with the restriction enzymes EcoRI and BclI, followed by electrophoresis in 0.8% agarose in TAE buffer. After excision from the gel, the largest band was purified using Gene Clean. The Boehringer Mannheim DNA Labeling and Detection kit (Nonradioactive) was used for these purposes according to the instructions of the manufacturer.

Segregational stability of plasmids

A single colony of LM0230 carrying the plasmid in question was inoculated from a selective plate into GM17 broth, grown up overnight and then twice grown up to stationary phase from a 250-times dilution. This corresponds to growth for approximately 20 generations. The culture was then spread to single colonies on GM17 plates, and 92 clones were scored for the presence of nisin resistance (pSW211 and pSW221) or for the presence of $Cm^r$ for pVS2 or $Em^r$ for pGKV1O.

Experimental section

EXAMPLE 1A

Construction of plasmid pVS34

*Lactococcus lactis* subsp. *lactis* biovar. *diacetylactis* SSD207, isolated from a dairy starter culture, comprises at least 12 plasmids ranging in size from 2 to more than 30 kbp. In hybridization experiments none of the SSD207 plasmids hybridized with pVS2, a typical broad host range vector based on a 2.1 kbp lactococcal plasmid pSH71. This strain was therefore screened for plasmid replication functions with a limited capacity for expression outside the lactic acid bacteria using the following method:

The 4.0 kbp ClaI fragment from plasmid pVS5 (Soile Tynkkynen, M.Sc. Thesis, University of Helsinki, Helsinki, Finland) containing the chloramphenicol resistance gene of a streptococcal plasmid pGB301 (Mol. Gen. Genet. 184, 115120 (1981)) was mixed with and ligated to the total plasmid DNA of SSD207 digested with ClaI. The ligation mixture was used to transform MG1614 protoplasts using selection for chloramphenicol resistance.

Thirty transformants were obtained from the ligation mixture, which contained about 1 μg of DNA. The majority of the transformants carried plasmids about 8 kbp in size, while the rest apparently contained randomly inserted extra ClaI-generated fragments. One clone was chosen for further studies, and was designated pVS34. The restriction map of this plasmid is presented in FIG. 1A. In DNA—DNA hybridization experiments the 4.1 kbp ClaI BclI fragment of pvs34 (containing the replication functions) hybridized with the approximately 28 kbp plasmid of SSD207.

In order to test whether any of the identified restriction sites of pVS34 interrupt the replication region of the plasmid, fusion plasmids with pBR322 were generated by linearizing pBR322 with either HindIII, ClaI or BamHI and ligating to pVS34 digested with HindIII, HpaII or XhoII, respectively. $E.$ $coli$ was transformed with these ligation mixtures using ampicillin selection. Transformants were tested on chloramphenicol (5 μg/ml) plates. Plasmid DNA from chloramphenicol resistant transformants were used to retransform MG1614 protoplasts. Only with the construction in which the HindIII ligation formed the hybrid plasmid no transformants were produced. With the rest, normal transformant frequencies (about $10^4$ chloramphenicol resistant clones/μg DNA) were obtained, and the plasmids extracted from the transformants had the expected sizes and restriction patterns. This, together with the successful use of the EcoRI site for cloning (see below), has led to the conclusion that at least part of the replication region of pVS34 is located within the 3.5 kbp EcoRI-ClaI restriction fragment.

EXAMPLE 1B

Host range of plasmid pVS34

To determine whether the host-range of the cloned replication function was indeed narrow, attempts were made to transform a number of taxonomically unrelated bacterial species with pVS34. In all these species it is known that the chloramphenicol resistance marker gene on pVS34 can be expressed (von Wright, A., S. Tynkkynen and M. Suominen. 1987, $Appl.$ $Environ.$ $Microbiol.$ 53, 1584–1588).

Transformation of $E.$ $coli$ AB259, $B.$ $subtilis$ 3G18, $Lb.$ $plantarum$ 755, and $S.$ $aureus$ RN451 was attempted using purified pVS34 DNA (from lactococcal preparative isolations). As positive controls parallel experiments were carried out using equal amounts of pVS2 (which contains the same chloramphenicol resistance gene as pVS34), and the transformant frequencies were compared. The results are presented in Table II. It can be seen that, besides $Lactococcus$ MG1614, pVS34 was only able to transform $Lb.$ $plantarum$ and, at a very low frequency, $S.$ $aureus$. The presence of pVS34 DNA could subsequently be demonstrated in $Lb.$ $plantarum$ and $S.$ $aureus$ transformants.

TABLE II

Transformation of different recipients by plasmids pVS2 and pVS34
Transformant frequency/μg of plasmid DNA

| Plasmid | Lactococcus lactis MG1614 | E. coli AB259 | B. Subtilis 3G18 | S. aureus RN451 | Lb. plantarum 755 |
|---|---|---|---|---|---|
| pVS2 | $1.0 \times 10^4$ | $1.0 \times 10^5$ | $2.6 \times 10^3$ | $3.2 \times 10^2$ | $1.4 \times 10^2$ |
| pVS2 cut and religated[a] | — | — | $2.0 \times 10^5$ | — | — |
| pVS34 | $1.0 \times 10^4$ | N. D. | N. D. | $3.3 \times 10^1$ | $5.7 \times 10^2$ |
| pVS34 cut and religated[a] | — | — | N. D. | — | — |

[a]Cutting and religation were performed in order to create plasmid multimers for $B.$ $subtilis$ transformations (see Materials and Methods).
— experiment not done, N. D. = no transformants detected The amount of DNA used varied from 5 to 100 ng per transformation depending on the transformation method and recipient (optimization was done using pVS2 as a model plasmid).

EXAMPLE 2A

Isolation of a nisin resistance determinant

The strain $Lactococcus$ $lactis$ subsp. $lactis$ 10.084, obtained from the collection maintained at the Danish Government Research Institute for Dairy Industry, was chosen as the donor of the nisin resistance gene because of its high level of production of nisin. As a consequence of this high level, the strain is also resistant to high levels of nisin, growing unhindered in concentrations of 1000 μg/ml, and 3000 μg/ml nisin having only a slight negative effect on the bacterial growth; see Table III.

TABLE III

Single-cell resistance of various lactococcal strains to nisin.
Relative number of colonies

| | concn. of nisin (iu per ml) | | | | | | |
|---|---|---|---|---|---|---|---|
| Strain | 0 | 10 | 100 | 500 | 1000 | 2000 | 3000 |
| L. lactis subsp. | | | | | | | |
| lactis 10.084 | +++ | +++ | +++ | +++ | +++ | ++ | ++ |
| MG1614 | +++ | 0 | 0 | | | | |
| MG1614(pNis) | +++ | +++ | +++ | +++ | +++ | ++ | ++ |
| LM0230 | +++ | 0 | 0 | | | | |

TABLE III-continued

Single-cell resistance of various lactococcal strains to nisin.
Relative number of colonies

| Strain | concn. of nisin (iu per ml) | | | | | | |
|---|---|---|---|---|---|---|---|
| | 0 | 10 | 100 | 500 | 1000 | 2000 | 3000 |
| LM0230(pVS2) | +++ | 0 | 0 | | | | |
| LM0230(pSW211) | +++ | +++ | +++ | +++ | +++ | ++ | ++ |
| LM0230(pSW221) | +++ | +++ | +++ | +++ | +++ | ++ | ++ |
| MG1614(pVS40) | +++ | +++ | +++ | +++ | +++ | ++ | ++ |

+++ approximately same number of colonies as on GM17 plates without nisin
++ approximately one log fewer colonies as on GM17 plates without nisin
0 no colonies
— not tested The strain 10.084 carries 5 or 6 plasmids, and starting with the total plasmid DNA of the strain, 2 rounds of transformation in MG1614 were carried out, followed each time by selection for nisin resistance. One of the resultant clones contained a single, 46 kbp-plasmid, which is denoted pNis/pSF01. As well as being Nis$^r$, strain MG1614(pNis/pSF01) is also Nip$^+$, Lac$^+$ and Prt$^+$ but cannot ferment sucrose (Table I).

The primary cloning of the nisin resistance gene from plasmid pNis/pSF01 was carried out by restricting about 0.8 μg pNis/pSF01 DNA and 2 μg pVS2 DNA with HindIII. After the vector had been treated with calf intestine phosphatase, both portions of DNA were freed of the enzymes by using Gene Clean, combined and ligated overnight at 14° C. One-half of the ligation mixture was used to transform MG1614 followed by selection for nisin resistance. Twenty-eight transformants were screened for Cm$^r$ and Em$^r$ and 26 of these showed the correct phenotype.

Eight of these clones were purified and their plasmid DNA isolated, cleaned with Gene Clean and restricted with HindIII. In all eight clones a 7.5 kbp fragment was present together with the vector. The plasmid DNA of one clone carrying only this fragment plus the vector was retransformed into LM0230. Preparative quantities of plasmid DNA, isolated via CsCl-ethidium bromide density gradients, were obtained from this clone, which is denoted LM0230 (pSW211). The phenotype of this organism (Table I and III) indicated that the cloned 7.5 kbp fragment only coded for nisin resistance and not for any of the other phenotypes of the plasmid pNis.

Figure 2A:
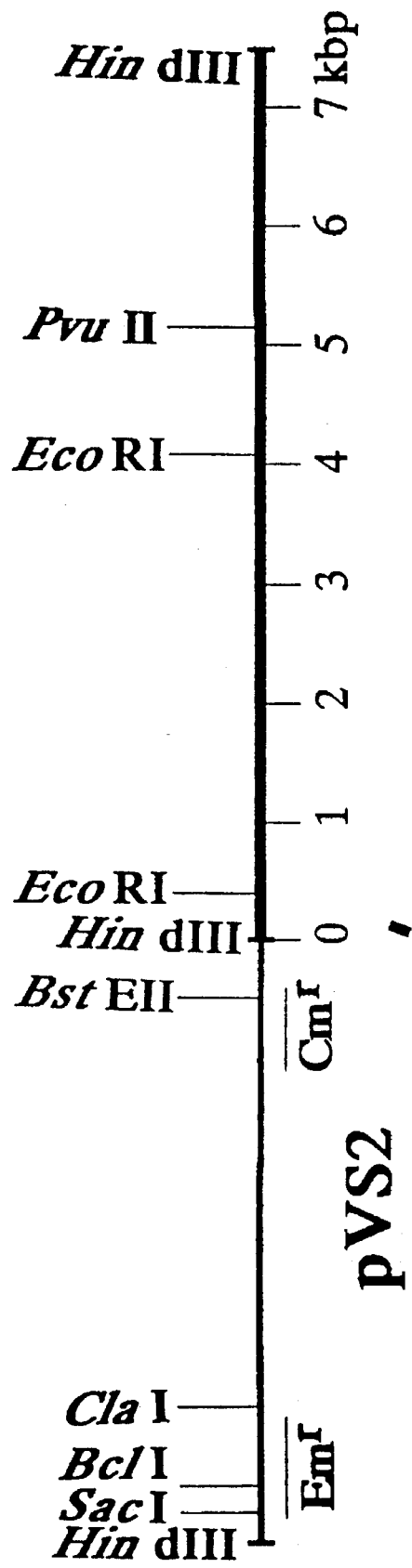
FIG. 2 (parts A & B) show restriction maps of a DNA fragment comprising a nisin resistance determinant isolated from plasmid pNis/pSF01 isolated from *Lactococcus lactis* subsp *lactis* 10.084 which fragment is located on pSW211 (A) and pSW221 (B), respectively. The restriction sites indicated on the DNA derived from pNis (bold line) were mapped using the particular plasmid on which they are located. The location of the nisin resistance determinant on pSW221 (cross-hatched area) is based on the observation that deletion of the smaller EcoRI—SaCI fragment results in a loss of resistance. pvs2 and pGKV10 (thin line) indicate DNA originating from plasmids with these designations.
Figure 2B:
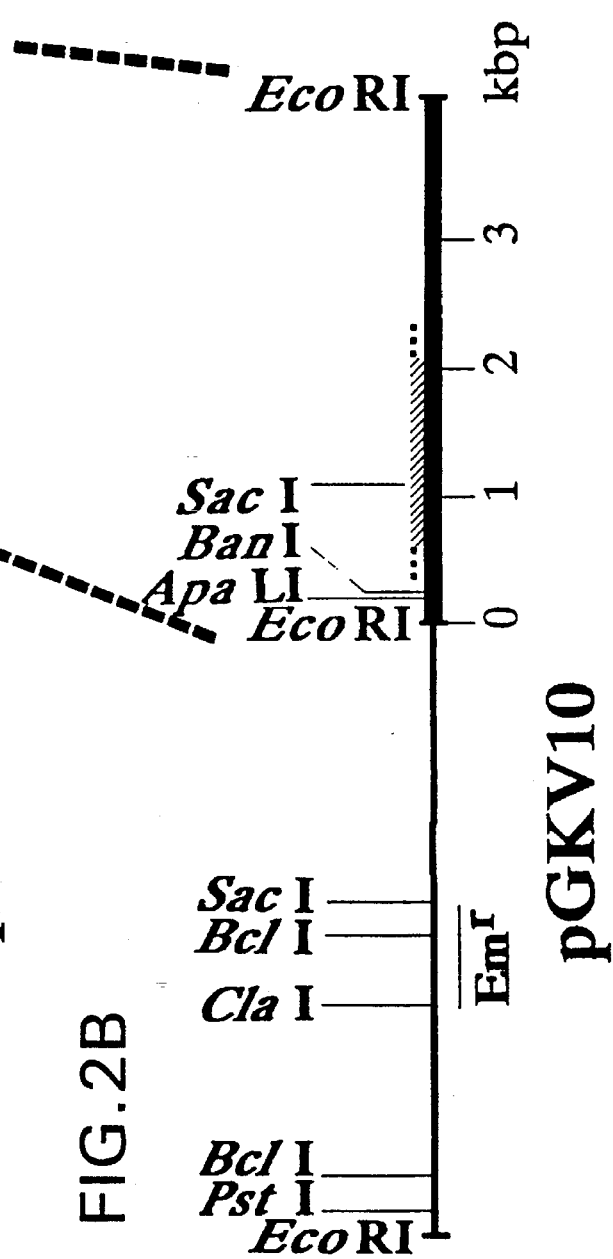

The restriction map of the primary, cloned fragment is shown in FIG. 2A. In order to reduce the size of the nisin resistance fragment, the EcoRI fragment was cut out of an agarose gel and subcloned onto the vector pGKV10. This construction is termed pSW221 (FIG. 2B) and has a phenotype identical to that of the entire HindIII fragment of pSW211.

Figure 3B:
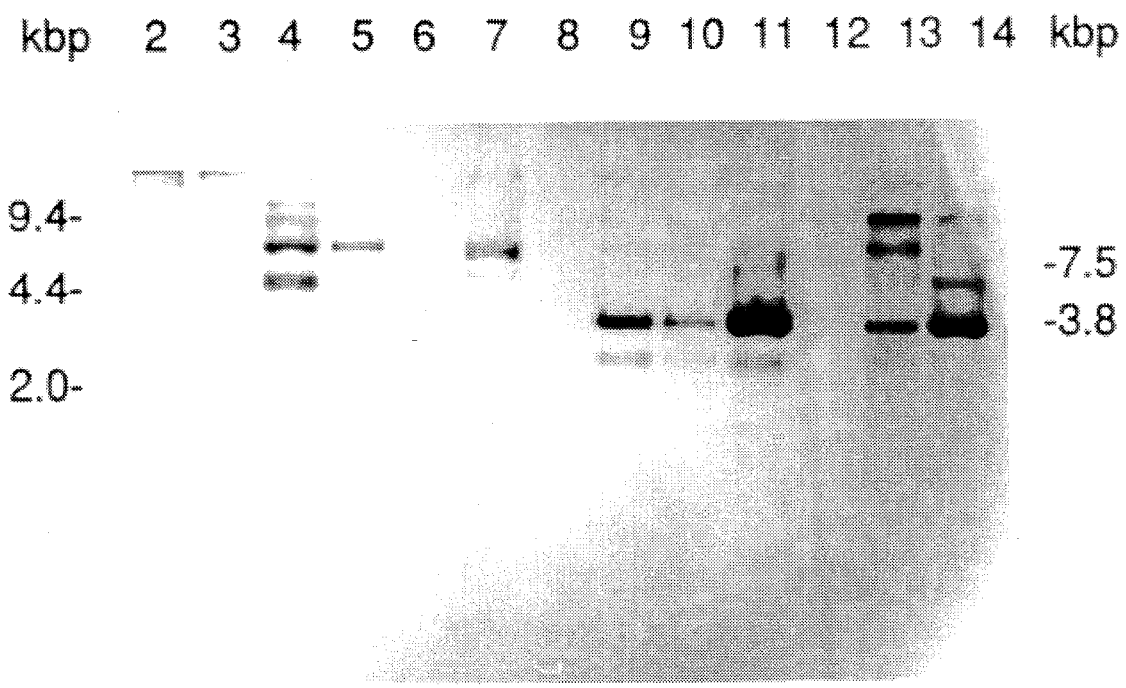

As shown in FIG. 3, a hybridization probe prepared from the isolated EcoRI fragment of pSW221 confirmed the presence of this fragment in one plasmid of the original wild type donor organism, in the isolated wild type plasmid pNis, and in the originally cloned HindIII fragment. This fragment showed no homology with the vector pVS2.

EXAMPLE 2B

Characterization of the nisin resistance determinant

Frequency of spontaneous nisin resistant mutants in laboratory strains

Before determining the suitability of a new resistance determinant for use as a one-step primary selectable marker in bacteria, one must demonstrate that the bacteria do not inherently possess appreciable resistance to the compound in question and that the bacteria will not spontaneously acquire resistance at a significant frequency. For the nisin resistance determinant as described in Example 2A, the lack of background resistance or of spontaneously arising resistance to nisin in two widely used laboratory strains was demonstrated as follows.

The frequency of spontaneous nisin resistant mutants was determined for the plasmid-free lactococcal strains MG1614 and LM0230. Cells of each strain grown in GM17 broth were harvested by centrifugation, resuspended in one-tenth the original volume sterile distilled water and plated in the appropriate dilutions on GM17 agar containing 0, 100 and 1000 iu/ml nisin. The plates were incubated at 30° C. and the colonies counted after 24 and 48 h. The frequencies at which Nisr colonies occurred even on 100 iu/ml nisin were at levels normally expected for spontaneous mutations and are within the frequencies acceptable for genetic experiments with the gene in question (Table IV).

TABLE IV

Frequency of spontaneous nisin resistant mutants arising in plasmid-free strains of L. lactis subsp. lactis after 24 and 48 h.

| Strain | Period of Incubation (h) | $^a$Frequency of Nis$^r$ colonies on GM17 + nisin plates concn. of nisin (μg pr. ml) | |
|---|---|---|---|
| | | 100 | 1000 |
| MG1614 | 24 | $1.8 \times 10^{-7}$ | $<7.9 \times 10^{-10}$ |
| | 48 | $3.4 \times 10^{-7}$ | $<7.9 \times 10^{-10}$ |
| LM0230 | 24 | $5.8 \times 10^{-8}$ | $<8.5 \times 10^{-10}$ |
| | 48 | $1.8 \times 10^{-7}$ | $<8.5 \times 10^{-10}$ |

$^a$Values are the average of frequencies determined in 2 independent experiments. No colonies were ever observed on plates containing 1000 μg nisin pr. ml.

Occurrence of nisin resistant organisms in two commercial dairy starter cultures To assess the usefulness of the Nis$^r$ determinant in genetic recombination of organisms in dairy practice, assessment was made of the occurrence of naturally nisin resistant organisms in two presently widely used commercial dairy starter cultures. The two starter cultures BOLL1 and D1 both comprising a multiplicity of strains were plated onto GM17 plates containing 100 and 1000 μg/ml nisin. The proportions of total cfu in the cheese starter BOLL1 which were Nis$^r$ on 100 and 1000 μg nisin per ml were $5.3 \times 10^{-4}$ and $5.3 \times 10^{-5}$, respectively. In the butter starter culture D1, $3.9 \times 10^{-1}$ and $1.3\times10^{-1}$ of total cfu were resistant to nisin at 100 and 1000 µg per ml, respectively.

Physiological confirmation of cloning of nisin resistance determinant

The data presented in Table III illustrate the level of sensitivity to nisin of strains used in the present specification, as well as the level of resistance conferred by a selectable marker according to the invention. These single cell resistances to nisin confirm that the cloned HindIII fragment of pSW211, as well as its EcoRI subclone (pSW221) code for the same high level of resistance as the genome of the original wild-type donor strain.

Experiments were carried out to investigate the effect of challenging exponentially growing sensitive cells and exponentially growing cells carrying a nisin resistance determinant with nisin. As illustrated in FIG. 4, 10 µg pr. ml nisin in GM17 broth caused a 4 log drop in the number of viable cells in the population carrying the vector pVS2 alone [LM0230(pVS2)]. A second addition of nisin 1 ½ h after the first caused an additional drop in viable cells of at least two logs. Six hrs after the start of the experiment fewer than 100 viable cells pr. ml culture were detected.

In the culture carrying the HindIII fragment [LM0230(pSW211)], the initial addition of 10 µg pr. ml nisin killed about 80% of the population, and the second addition of the bacteriocin also produced a small drop in the population size.

In order to examine the genetic complement of the population inoculated with LM0230(pSW211) and still surviving 15 min. after the first addition of nisin, the phenotypes of 92 colonies from the GM17 plates representing the bottom of the first drop in the curve at 1 ¼ h (indicated by * on curve in FIG. 4) were screened. Three of the 92 clones were $Nis^s$ $Cm^s$ $Em^s$, and small-scale plasmid preparations showed that all three of these clones had lost all plasmid DNA. This result indicates that the recombinant plasmid is segregationally somewhat unstable but not more unstable than could be accounted for by the increased size of the constructed plasmids relative to the vectors alone.

The use of a nisin resistance determinant as a selectable marker

In the following transformation experiments, the ability to select for transformants using a nisin resistance determinant according to the present invention was compared with the ability to select for transformants using the traditional antibiotic resistance marker on the very same DNA molecule. The relative efficiency of selection, or selectability, of the nisin resistance determinant in transformation experiments was defined as the transformant frequency upon selection for nisin resistance relative to the transformant frequency upon selection for $Cm^r$ or $Em^r$. For the recombinant plasmid pSW211 nisin selection was calculated relative to $Cm^r$, and for pSW221 the selection was calculated relative to $Em^r$. The $Cm^r$ gene of the vector pVS2 derives from the plasmid pGB301 [*Appl. Environ. Microbiol.* 53. 1584–1588 (1987)] and the $Em^r$ gene of pGKVl0 is taken from pE194 (*Appl. Environ. Microbiol.* 50, 540–542 (1985)).

Under the conditions chosen the strain LM0230 and MG1614 were about equally competent when used as recipients of the plasmid pVS2 (Table V). Moreover, both strains were transformed at equal but significantly lower frequencies by the 2 nisin resistant recombinant plasmids investigated in this study when selection is carried out for their $Cm^r$ and $Em^r$ resistances. The reductions in transformant frequencies relative to pVS2 appeared to correspond with the increased sizes of the plasmids.

When selection was conducted for the studied $Nis^r$ determinant itself, transformants of LM0230 were selected with the same effiency as when the other markers on the recombinant plasmids are selected. However, when nisin resistance was selected in MG1614, transformants were only one-tenth as efficiently selected relative to the other resistance on the plasmids.

TABLE V

Relative efficiency of selection for the nisin resistance determinant in transformation experiments in lactococci.

| Recipient | Plasmid[a] | $Cm^r$ or $Em^r$ transformant frequency[b] (transformants pr. µg DNA) | Relative efficiency of selection for $Nis^r$ [c] |
|---|---|---|---|
| PROTOPLAST TRANSFORMATION | | | |
| MG1614 | pVS2 | $1.8 \times 10^5$ | n.a.[d] |
| | pSW211 | $3.9 \times 10^3$ | 0.09 |
| | pSW221 | $4.0 \times 10^4$ | 0.12 |
| LM0230 | pVS2 | $2.6 \times 10^5$ | n.a. |
| | pSW211 | $5.9 \times 10^3$ | 0.86 |
| | pSW221 | $3.7 \times 10^4$ | 1.0 |
| ELECTROPORATION | | | |
| LM0230 | pSW211 | $3.2 \times 10^6$ | 0.56 |
| | pVS39 | $3.2 \times 10^6$ | 0.34 |

[a]All plasmid DNA was isolated from LM0230 and purified through a CsCl density gradient.
[b]$Cm^r$ and $Em^r$ transformant frequencies are the average of at least 2 experiments and calculated on the basis of transformants arising on Cm plates (pVS2 and pSW211) or Em plates (pSW221).
[c]The relative efficiency of selection for the $Nis^r$ determinant is defined as the transformant frequency upon selection for $Nis^r$ divided by the transformant frequency upon selection either for $Cm^r$ or $Em^r$.
[d]n.a.: not applicable.

The studied nisin resistance determinant is very useful as a selectable marker due to at least two properties. In the first place, the $Nis^r$ determinant codes for a high level of resistance in the lactococci tested. This results in resistance-bearing lactic acid bacterial strains tolerating more than 100 times as much nisin as sensitive ones. Klaenhammer and Sanozky, *J. Gen. Microbiol,* 131, 1531–1541 (1985) were unable to perform an actual selection for the $Nis^r$ determinant they studied because of a high frequency of spontaneous $Nis^r$ mutants. These workers also used the strain LM0230 as a recipient in conjugation experiments but the selection medium contained only 100 ng nisin pr. ml apparently due to a significantly lower level of resistance conferred by their nisin resistance determinant. This complication does not arise when using the nisin resistance determinant of the present invention due to the fact that the high level of resistance allows direct primary selection of transformants at concentrations of the bacteriocin where resistant colonies arise only at frequencies typical of true spontaneous mutants.

A second characteristic that contributes to the suitability of the presently studied $Nis^r$ determinant as a selectable marker is the apparently constitutive expression of the resistance. In the strain LM0230 the expression of the gene(s) does not seem to require any more induction than does the two pharmaceutical antibiotic resistance genes used in the present example as a basis of comparison of selectability. On the other hand, the strain MG1614 is only one-tenth as transformable by the $Nis^r$ determinant as by the antibiotic resistance genes.

Effect on segregational stability of the nisin resistance-encoding fragment

To investigate the extent of instability of the two nisin resistant recombinant plasmids studied, as well as of the pSW211 and pSW221 vectors used in the constructions hereof, the strain LM0230 carrying each plasmid was grown for about 20 generations in the absence of selective pressure for the plasmids. While no clones cured of pVS2 or pGKV10 could be detected, 2.2% of the colonies phenotypically scored for pSW211 had lost the plasmid, while 4.4% of those scored for pSW221 had lost the phenotype conferred by this plasmid.

Indeed, plasmid preparations of the 2 clones cured of pSW211 showed no plasmid DNA, and 3 of the 4 clones cured of the pSW221 phenotype also lacked plasmid DNA. Apparently, the cloned HindIII-fragment and its EcoRI subclone have only very small negative effects on the segregational stability of the vectors on which they are cloned. This result is essential when the resistance determinant is to be used on food grade vectors in the dairy industry. Here very large concentrations of cells are handled in the various productions and are grown in the absence of any sort of selection pressure other than that provided by milk as a growth medium.

EXAMPLE 3

Construction of plasmid pVS39

Figure 1B:
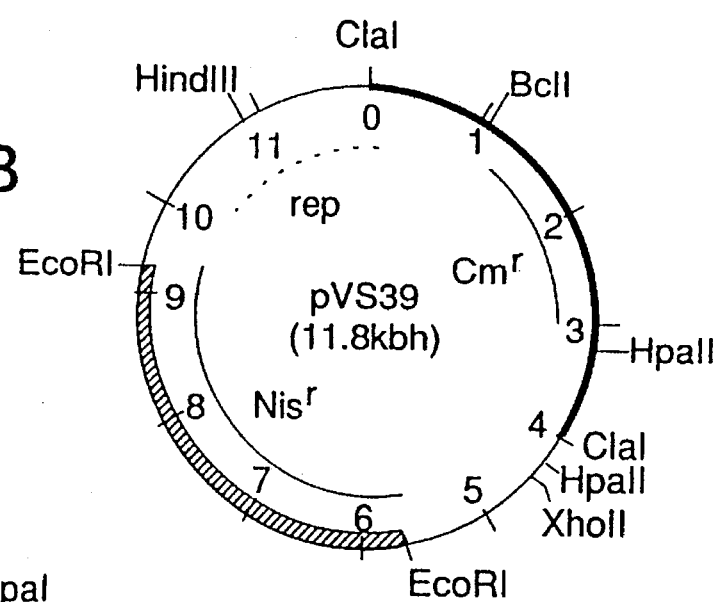
FIG. 1B is a partial restriction map of an intermediate plasmid pVS39 which in addition to the DNA of pVS34 comprises a 3.7 kb EcoRI DNA fragment from the plasmid pNis which is isolated from *Lactococcus lactis* subsp *lactis* 10.084 and which fragment has been inserted in pSW211 (hatched area).

The 3.7 kbp EcoRI fragment coding for nisin resistance from plasmid pSW211 was ligated to the single EcoRI site of pVS34. MG1614 protoplasts were transformed with this ligation mixture selecting for chloramphenicol resistance. Transformants were tested for nisin resistance and analysed for plasmid content. The restriction map of one of the nisin-chloramphenicol doubly resistance plasmids, denoted pVS39, is shown in FIG. 1B.

EXAMPLE 4

Construction of plasmid pVS40

Figure 1C:
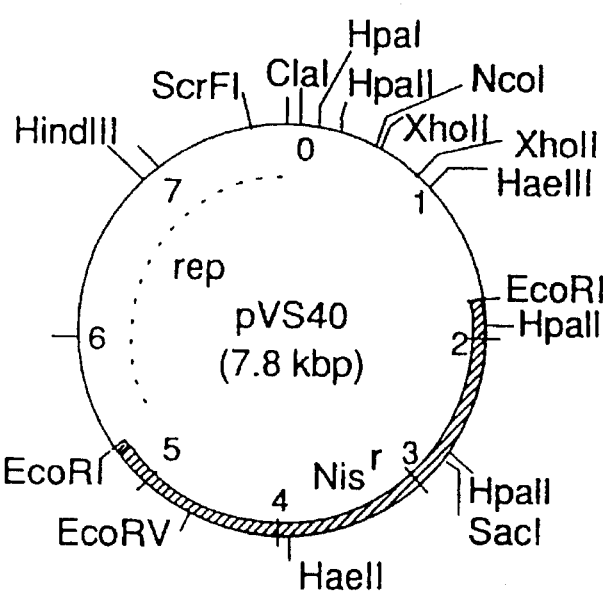
FIG. 1C is a partial restriction map of the plasmid pVS40.

In order to construct a nisin resistance plasmid containing only lactic acid bacterial DNA, the streptococcal chloramphenicol resistance gene was excised from pVS39. This was effected by digesting pVS39 with ClaI, isolating the 7.8 ClaI fragment comprising both the nisin resistance and replication regions of pVS39 from an agarose gel and self-ligating the fragment. This DNA was used together with similarly topologically relaxed plasmid DNA (coding for chloramphenicol resistance) to transform MG1614 protoplasts. The plasmid pVS1 used in the co-transformation was first linearized with ClaI and self-religated. The ratio of the 7.8 kbp ClaI fragment of pVS39 to pVS1 DNA in the cotransformation mixture was about 3 to 1. Chloramphenicol resistant transformants were selected, and these were further tested for their resistance to nisin. Three doubly resistant clones were found among the twenty tested, and they all contained two plasmids corresponding in size to intact pVS1 and covalently closed supercoiled 7.8 kbp DNA. One of the clones was chosen for novobiocin curing of pVS1. Nisin (500 iu/ml) was used in both agar layers of novobiocin gradient plates. Of 100 purified single colonies picked from the novobiocin plates, one proved to be nisin resistant and chloramphenicol sensitive. It was found to contain a single plasmid representing the self-ligated 7.8 kbp ClaI fragment of pVS40 (FIG. 1C).

Upon testing the segregational stability of pVS40 in the strain M0230, it was found that 16% of the clones tested had become nisin sensitive. This result together with those described above in Example 2B for plasmids pSW211 and pSW221 may indicate that the replication function of pVS40 is not completely stable, and that this plasmid might disappear from the bacterial population unless selective pressure for its maintenance is present. However, the Lac-positive construction of pVS40 described in Example 5 has been shown to be completely segregationally stable when the cells are grown in a medium with lactose as the carbon source.

EXAMPLE 5

Cloning of lactose fermentation gene(s) into pVS40

One of the two XhoII sites of pVS40 has been successfully used in cloning the lactose fermentation genes on the BclI B fragment of a derivative of the lactococcal plasmid pLP712 [Gasson, Hill and Anderson; Molecular genetics of metabolic traits in lactic streptococci in Ferretti and Curtiss (ed.), Streptococcal genetics, American Society for Microbiology, Washington D.C. (1987)]. Isolation of Lac+ transformants was performed by one-step primary selection for nisin resistance as described above followed by screening on lactose fermentation indicator plates. The Lac$^+$ Nis$^r$ phenotype has been stable in further transformations with DNA isolated from the original clones. Segregationally, the recombinant plasmid comprising pVS40 and the inserted Lac$^+$ fragment is indeed more stable than pVS40 itself, showing only 9% Nis$^s$ clones as compared to 16% for pVS40 (Example 4).

We claim:

1. A plasmid vector that replicates in a lactic acid bacteria host cell, but not in *Escherichia coli* and *Bacillus subtilis* host cells, comprising in an operable linkage:

a) a first DNA coding for an origin of replication functional in said lactic acid bacteria host cell but not in said *Escherichia coli* and *Bacillus subtilis* host cells;

b) a second DNA conferring nisin resistance in said lactic acid bacteria host cell but not in said *Escherichia coli* host cell; and c) a third DNA coding for one or more restriction sites; wherein said first, second, and third DNAs are isolated from lactic acid bacteria or plasmids therefrom.

2. The plasmid vector of claim 1, wherein said first and second DNAs are isolated from different plasmids.

3. The plasmid vector of claim 1, wherein said second DNA confers nisin resistance in said lactic acid bacteria host cell to at least 200 iu/ml nisin.

4. The plasmid vector of claim 3, wherein said second DNA confers nisin resistance in said lactic acid bacteria host cell to at least 500 iu/ml nisin.

5. The plasmid vector of claim 3, wherein said second DNA confers nisin resistance in said lactic acid bacteria host cell to at least 1000 iu/ml nisin.

6. The plasmid vector of claim 3, wherein said second DNA confers nisin resistance in said lactic acid bacteria host cell to at least 2000 iu/ml nisin.

7. The plasmid vector of claim 3, wherein said second DNA confers nisin resistance in said lactic acid bacteria host cell to at least 3000 iu/ml nisin.

8. The plasmid vector of claim 1 or 2, wherein said first and second DNAs are isolated from wild-type plasmids isolated from *Lactococcus* spp.

9. The plasmid vector of claim 8, wherein said first DNA is isolated from a wild-type plasmid isolated from *Lactococcus* subsp. *lactis* biovar *diacetylactis*.

10. The plasmid vector of claim 9, wherein said first DNA is isolated from a wild-type plasmid isolated from *Lactococcus* subsp. *lactis* biovar *diacetylactis* SSD207.

11. The plasmid vector of claim 8, wherein said second DNA is isolated from a wild-type plasmid isolated from *Lactococcus* subsp. *lactis*.

12. The plasmid vector of claim 11, wherein said second DNA is isolated from a wild-type plasmid isolated from *Lactococcus* subsp. *lactis* 10.084.

13. The plasmid vector of claim 1 or 2 which is pVS40.

14. The plasmid of claims 1, 2 or 3, wherein a fourth DNA is inserted into said restriction site of said third DNA, and wherein said fourth DNA comprises at least one gene coding for a desired gene product operably linked to a promoter such that said gene is transcribed in said lactic acid bacteria host cell.

15. The recombinant plasmid vector of claim 14, wherein said fourth DNA is isolated from a lactic acid bacterium or a plasmid therefrom.

16. The plasmid vector of claim 14, wherein said fourth DNA comprises one or more genes encoding desired products selected from the group consisting of genes encoding enzymes and genes encoding products conferring phage resistance.

17. The plasmid vector of claim 14, wherein said one or more genes encode gene products that convert lactose to lactic acid.

18. A food starter culture, comprising a culture of a lactic acid bacteria host cell containing the plasmid vector of claim 14.

19. The food starter culture of claim 18, which is a dairy starter culture.

20. The food starter culture of claim 19, wherein the culture is in a frozen or freeze-dried form.

21. The food starter culture of claim 18, wherein said lactic acid bacterium host cell is selected from the group consisting of *Streptococcus* spp., *Lactococcus* spp., *Lactobacillus* spp., *Bifidobacterium* spp., *Leuconostoc* spp., *Propionibacterium* spp., and *Pedicoccus* spp.

* * * * *